United States Patent
Baleux et al.

(10) Patent No.: US 9,907,860 B2
(45) Date of Patent: Mar. 6, 2018

(54) CONJUGATED MOLECULES COMPRISING A PEPTIDE DERIVED FROM THE CD4 RECEPTOR COUPLED TO AN ANIONIC POLYPEPTIDE FOR THE TREATMENT OF AIDS

(71) Applicants: INSTITUT PASTEUR, Paris (FR); COMMISSARIAT A L'ENERGIE ATOMIQUE ET AUX ENERGIES ALTERNATIVES, Paris (FR); UNIVERSITE PARIS-SUD, Orsay (FR); UNIVERSITE GRENOBLE ALPES, St Martin d'heres (FR); CENTRE NATIONAL DE LA RECHERCHE SCIENTIFIQUE (CNRS), Paris (FR)

(72) Inventors: Francoise Baleux, Paris (FR); Hugues Lortat-Jacob, Montbonnot (FR); David Bonnaffe, Paris (FR); Yves-Marie Coic, Meudon (FR)

(73) Assignees: INSTITUT PASTEUR, Paris (FR); COMMISSARIAT A L'ENERGIE ATOMIQUE ET AUX ENERGIES ALTERNATIVES, Paris (FR); UNIVERSITE PARIS-SUD, Orsay (FR); UNIVERSITE GRENOBLE ALPES, St Martin d'heres (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/516,296

(22) PCT Filed: Oct. 23, 2015

(86) PCT No.: PCT/EP2015/074598
§ 371 (c)(1),
(2) Date: Mar. 31, 2017

(87) PCT Pub. No.: WO2016/062854
PCT Pub. Date: Apr. 28, 2016

(65) Prior Publication Data
US 2017/0326246 A1 Nov. 16, 2017

(30) Foreign Application Priority Data
Oct. 24, 2014 (EP) .................... 14306698

(51) Int. Cl.
*A61K 38/00* (2006.01)
*C07K 14/00* (2006.01)
*A61K 47/64* (2017.01)
*C07K 14/73* (2006.01)

(52) U.S. Cl.
CPC ...... *A61K 47/645* (2017.08); *C07K 14/70514* (2013.01); *A61K 38/00* (2013.01)

(58) Field of Classification Search
None
See application file for complete search history.

(56) References Cited

U.S. PATENT DOCUMENTS

2009/0285798 A1* 11/2009 Vita ................ C07K 14/70514
424/130.1

FOREIGN PATENT DOCUMENTS

| WO | 2008/015273 A1 | 2/2008 |
| WO | 2009/098147 A2 | 8/2009 |
| WO | 2012/126833 A1 | 9/2012 |

OTHER PUBLICATIONS

Baleux et al, "A synthetic CD4-heparan sulphage glycoconjugate inhibits CCR5 and CXCR4 HIV-1 attachment and entry," Nat. Chem. Bio., 2009, 5(10), 743-748.
Tamalet et al., "Resistance of HIV-1 to multiple antiretroviral drugs in France: a 6-year survey (1997-2002) based on an analysis of over 7000 genotypes," AIDS., 2003, Nov 7; 17(16) :2383-8.
Huang CC et al., "Scorpion-Toxin Mimics of CD4 in Complex with Human Immunodeficiency Virus gp120: Crystal Structures, Molecular Mimicry, and Neutralization Breadth," Structure, 2005, May, 13(5):755 -68.
Van Herrewege et al., "CD4 mimetic miniproteins: potent anti-HIV compounds with promising activity as microbicides," J. Antimicrob. Chemother, 61(4), 818-826,2008.
Lepelley et al., "Innate Sensing of HIV-Infected Cells," PLoS Pathog 2011, 7:e1001284.
Malbec et al., "Broadly neutralizing antibodies that inhibit HIV-1 cell to cell transmission," J. Exp. Med., 2013, 210:2813-2821.

* cited by examiner

*Primary Examiner* — Jeanette Lieb
(74) *Attorney, Agent, or Firm* — Arrigo, Lee & Guttman LLP

(57) ABSTRACT

This invention relates to a conjugated molecule comprising a peptide derived from the CD4 receptor coupled to an organic molecule by means of a linker as well as a process for its preparation. Said organic molecule comprises a 5 to 21 amino acid anionic polypeptide. Such a conjugated molecule can be used in antiviral treatment, namely in the treatment of AIDS.

20 Claims, 8 Drawing Sheets

A

B

A

B

CONJUGATED MOLECULES COMPRISING A PEPTIDE DERIVED FROM THE CD4 RECEPTOR COUPLED TO AN ANIONIC POLYPEPTIDE FOR THE TREATMENT OF AIDS

This invention relates to a conjugated molecule comprising a peptide derived from the CD4 receptor and an organic molecule which is an anionic polypeptide. Such a conjugated molecule can be used in antiviral treatment, namely in the treatment of AIDS. This invention further relates to processes for the preparation of the conjugated molecule.

Triple therapies combining nucleoside (NRTI), non-nucleoside (NNRTI) and/or protease inhibitors (PI) result in a reduction in viral charge beneath levels of detection in a large number of seropositive HIV patients. These therapies target reverse transcription and proteolysis at the same time. Their efficacy has led to a substantial decrease in the number of deaths resulting from HIV infection. Unfortunately, about 80% of the patients show genotypes with antiviral resistance and, more worryingly, 45.5% of viral populations are resistant to NRTI/PI combinations while 26% are resistant to a combination of three anti-HIV classes (Tamalet et al., AIDS. 2003 Nov. 7; 17(16):2383-8). This observation is particularly disturbing since the adverse effects of long-term triple therapy treatment (lipoatrophy, lipodystrophy, hypertriglyceridaemia, hypercholesterolaemia, neuropathy, etc.) found in 70% of patients receiving the treatment result in poor compliance and "sudden" discontinuation of treatment which often leads to resistance. The development of less severe forms of treatment with fewer adverse effects and without cross-resistance is therefore a priority despite the large number of currently available medications on the market. With this in mind, it is essential to target HIV replication steps other than reverse transcription and proteolysis.

Entry of a virus into a cell is a crucial step in the viral infection cycle. This process is divided into two phases: first, the virus interacts with specific host receptors at the cell surface, followed by penetration of the viral genetic material into the target cell. With HIV, the molecular partners involved in the mechanisms of adhesion and entry are well established. The gp120 viral envelope glycoprotein essentially determines the virus/cell interaction complex, by binding to a transmembrane glycoprotein of the host cell, CD4. This interaction leads to a conformational change in gp120 which exposes a particular epitope, called CD4-induced (CD4i), thus creating a binding site for chemokine receptors (essentially CCR5 and CXCR4). CCR5 and CXCR4 therefore act as gp120 co-receptors at the cell surface. This second interaction leads to re-organization of the gp120/gp41 protein complex and initiation of cell/virus membrane fusion.

The cellular tropism of the HIV virus is defined by the type of co-receptor used. So-called X4 or <<T-tropic>> viruses tend to infect more specifically cell lines expressing CXCR4 at their surface, such as the T lymphocytes. So-called R5 or <<M-tropic>> viruses use co-receptor CCR5 and mainly infect macrophages and monocytes. The presence of R5 or X4 viruses is generally associated with quite distinct stages of AIDS development (asymptomatic phase for R5, appearance of X4 virus often linked to unfavourable evolution outcome of the disease, suggesting that use of co-receptor CXCR4 is an important factor in the pathogenesis of AIDS). As the structural determinants for recognition of CCR5 and CXCR4 are carried by gp120, the R5 and X4 viruses represent two separate targets.

It was shown in international patent application WO 2008/015273 that particular activated peptides derived from the CD4 receptor can react selectively with organic molecules affording chemically defined covalent conjugates. This activation requires the insertion of one and only one residue of the amino acid lysine in a defined position in the sequence of the peptide derived from the CD4 receptor. This insertion allows the coupling of organic compounds through linkers and chemistries after the miniCD4 synthesis and purification.

Numerous potential antiviral derivatives, consisting of conjugated molecules comprising a CD4 peptide specifically coupled to polyanionic heparan sulphate (HS) by means of a linker were disclosed in WO 2009/098147. These conjugates show potent antiviral activity. The use of HS was motivated by the presence of at least two different HS recognition sites in gp120, namely the V3 variable loop and the site induced by CD4 (CD4i): the CD4 moiety of the mCD4-HS is thought to trigger conformational changes in gp120 by direct interaction, thus resulting in exposure of the CD4i epitope, with which the covalently bound HS can then interact, thereby impairing HIV virus infection of X4 and R5 cell lines.

This approach consisting in inhibiting viral attachment to cells is therapeutically advantageous, since it directly targets the virus and not the cells themselves. It is therefore devoid of the cellular effects observed with medication which binds to co-receptors. In addition, in view of the preservation of the sites involved as a function of various viral tropisms, the compounds according to the invention should interact with the gp120 of different viral isolates. While it might be misleading to think that resistance will never arise, it can nevertheless be expected that it should occur at a much lower rate than with other treatments. Indeed, the CD4 site of gp120 has to remain intact in order to continue to bind to CD4, like the basic residues involved in binding to the polyanionic polysaccharide for interaction with the co-receptors. Mutation in any of these two sites should indeed result in a virus with reduced infectivity.

Polyanions covalent coupling to miniCD4 peptides greatly enhances miniCD4 peptides HIV antiviral activity. Such bifunctionnal compounds, mCD4-HS12 and mCD4-P3YSO3, inhibit HIV entry and replication at low nanomolar concentration of not only laboratory-adapted strain but also of clinical strains (see e.g., WO2012/126833).

DESCRIPTION

The present inventors have now developed new conjugates comprising miniCD4 peptides and anionic polypeptides, which display enhanced HIV antiviral activity, with an activity in the picomolar range on the viral strains tested to date, independently of the co-receptor usage R5 or X4.

According to a first aspect, the invention covers a conjugated molecule comprising a peptide derived from the CD4 receptor, said peptide being coupled to an organic molecule by means of a linker, wherein:
the said peptide derived from the CD4 receptor comprises the following general sequence (I):

$$\text{Xaa}^f\text{-P1-Lys-Cys-P2-Cys-P3-Cys-Xaa}^g\text{-Xaa}^h\text{-Xaa}^i\text{-Xaa}^j\text{-Cys-Xaa}^k\text{-Cys-Xaa}^l\text{-Xaa}^m, \quad \text{(I)}$$

in which:
P1 represents 3 to 6 amino acid residues, and advantageously 3 amino acid residues,
P2 represents 2 to 4 amino acid residues,
P3 represents 6 to 10 amino acid residues, Xaa$^f$ represents N-acetylcysteine (Ac-Cys) or thiopropionic acid (TPA),
Xaa$^g$ represents Ala,
Xaa$^h$ represents D-proline (p),
Xaa$^i$ represents Thr,
Xaa$^j$ represents biphenylalanine (Bip), phenylalanine, [beta]-naphthylalanine or 4-cyclohexylmethoxy-L-phenylalanine (U$_1$),
Xaa$^k$ represents Thr or Ala,
Xaa$^l$ represents Gly, Val or Leu, and
Xaa$^m$ represents —NH$_2$ or —OH,
the amino acid residues in P1, P2 and P3 being natural or non-natural, identical or different, said residues of P1, P2 and P3 being all different from the Lys residue and P1, P2 and P3 having a sequence in common or not, and
the said organic molecule comprises
an anionic polypeptide consisting of 5 to 21, advantageously 10 to 17, and preferably 13 amino acid residues being natural or non-natural, identical or different, wherein at least 3, notably 3 to 15, such as 3 to 13 amino acids are negatively charged, and
a molecular group A-Z, wherein:
A comprises a group chosen between the groups of formula —CO(CH$_2$)$_p$—NH—CO—(CH$_2$)$_q$—, —CO(CH$_2$—CH$_2$)—(O—CH$_2$—CH$_2$)$_p$—NH—CO—(CH$_2$)$_q$—, —CO(CH$_2$)$_p$—NH—CO—(CH$_2$—CH$_2$—O)$_q$—(CH$_2$—CH$_2$)— and —CO(CH$_2$—CH$_2$)—(O—CH$_2$—CH$_2$)$_p$—NH—CO—(CH$_2$—CH$_2$—O)$_q$—(CH$_2$—CH$_2$)—, wherein p represents an integer comprised between 1 and 10 and q represents an integer comprised between 1 and 10, and advantageously A represents a group of formula —CO(CH$_2$)$_p$—NH—CO—(CH$_2$)$_q$— and preferably —CO(CH$_2$)$_3$NH—CO(CH$_2$)$_2$— and
Z represents a halogen atom, a thiol or a maleimide group,
wherein the first carbonyl group of A is coupled to the N-terminal end of the anionic polypeptide,
wherein the said linker is covalently bound at one of its extremity to the free amino group (—NH$_2$) of the amino acid residue Lys present in general sequence (I) of the said peptide derived from the CD4 receptor, and is covalently bound at its other extremity to the Z group of the said organic molecule when Z is a thiol or a maleimide group or to the A group of the said organic molecule when Z is a halogen atom, Z being eliminated in this last case.

Preferably, P3 comprises at least one basic amino acid, said basic amino acid being even more preferably arginine. The presence of basic residues in this portion of the CD4 receptor fragment contributes to its binding to the gp120 protein. The inventors therefore prefer to introduce at least one basic amino acid into P3, preferably arginine. This maintains thus a basic moiety which is not reactive at derivation at pH 7-8 but which has been found to be useful for the binding of miniCD4 peptide to the gp120 protein. More preferably, the first amino acid residue at the NH$_2$ end of P3 is an arginine, since the inventors have shown that it greatly enhances the miniCD4 peptides HIV antiviral activity.

In this application, the terms "miniCD4 peptide", "CD4 peptide" and "miniCD4" are used interchangeably to designate the peptide derived from the CD4 receptor comprising or consisting of general sequence (I) defined above.

As disclosed in WO 2009/098147, it is required that the miniCD4 peptide of the invention contains one and only one lysine (Lys) amino acid residue, and that said lysine is in the position as defined in general sequence (I). The Cys residues in general sequence (I) allow the formation of three disulphide bridges needed for folding back of miniCD4. Thiopropionic acid (TPA), when it is in the N-terminus position of the peptide of general sequence (I), makes it possible to reduce hindrance in N-ter and overcome the presence of an amine group. Thus, according to a preferred embodiment, Xaa represents TPA in general sequence (I).

Bip increases contact with glycoprotein gp120 in the cavity where the Phe 43 of CD4 receptor is lodged. Thus, in a preferred embodiment, Xaa$^j$ represents Bip. Nevertheless, it may be advantageous to have Phe as Xaa$^j$ in general sequence (I), since a structural analysis suggests that such a miniCD4 may mimic CD4 efficiently (Huang C C et al., Structure. 2005 May; 13(5):755-68). Thus according to another preferred embodiment, Xaa$^j$ represents Phe. It is however even more advantageous to have a flexible cyclohexylmethoxy group in the para-position of the phenylalanine, because the resulting miniCD4 has an even higher affinity for the conserved and vulnerable Phe43-cavity in gp120 (Van Herrewege et al., J. Antimicrob. Chemother, 61(4): 818-826, 2008). Therefore, more preferably, Xaa$^j$ represents 4-cyclohexylmethoxy-L-phenylalanine (U$_1$).

The peptide of general sequence (I) derived from the CD4 receptor forms an alpha helix structure followed by a beta sheet. The amino acids Xaa$^g$-Xaa$^h$-Xaa$^i$-Xaa$^j$-Cys-Xaa$^k$-Cys-Xaa$^l$ participate in a major way to the binding to gp120. These peptides display an IC$_{50}$ (affinity for gp120) similar to those of sCD4 (soluble CD4).

The CD4 peptide of the invention can be prepared by conventional solid phase chemical synthesis techniques, for example according to the Fmoc solid phase peptide synthesis method ("Fmoc solid phase peptide synthesis, a practical approach", edited by W. C. Chan and P. D. White, Oxford University Press, 2000) and/or by genetic recombination.

Preferably, the said CD4 peptide is chosen from the group consisting of sequences SEQ ID NO: 1, SEQ ID NO: 2, SEQ ID NO: 20 and SEQ ID NO: 21, preferably chosen from the group consisting of sequences SEQ ID NO: 1 and SEQ ID NO: 2. More preferably, the CD4 peptide of the invention has the sequence represented by SEQ ID NO: 1.

The term "Linker" refers in the present invention to a linker obtained by the coupling of a bifunctional compound, as defined below, with a peptide derived from the CD4 receptor and the organic molecule. Thus, the length of the linker varies as a function of the bifunctional compounds used.

In particular, the linker will be advantageously chosen among:

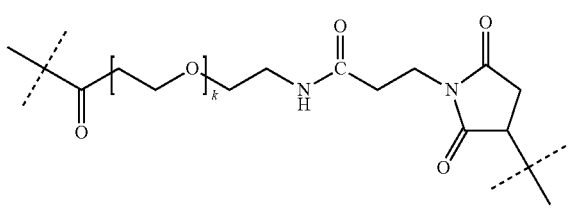

with k representing an integer comprised between 2 and 24, and being advantageously 2, 4, 8 or 12,

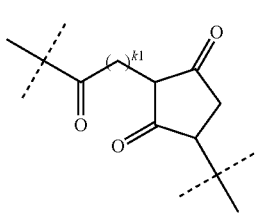
with k1 representing an integer comprised between 1 and 10, thus equal to 1, 2, 3, 4, 5, 6, 7, 8, 9 or 10, and advantageously equal to 1, 2, 3, 5 or 10,
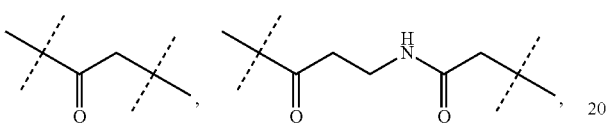
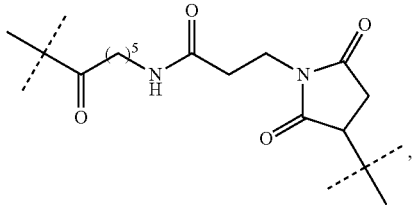
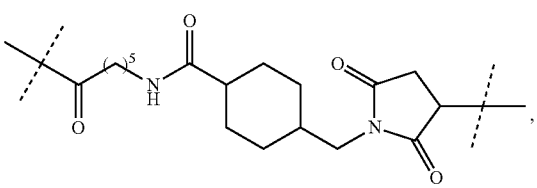
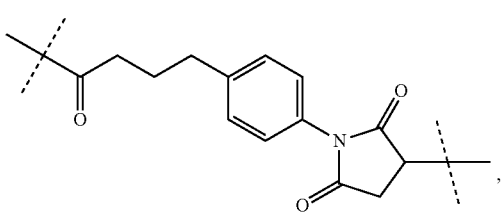
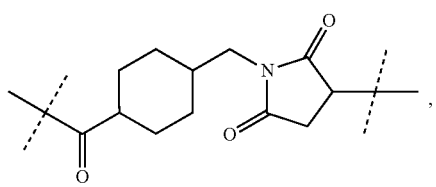
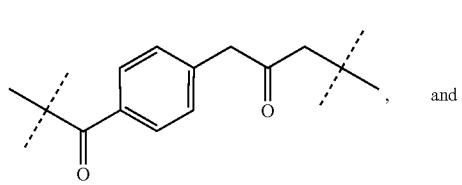, and
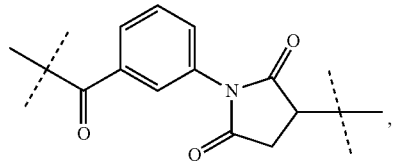
when Z represents a thiol group, and among:
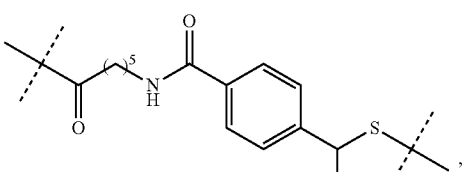
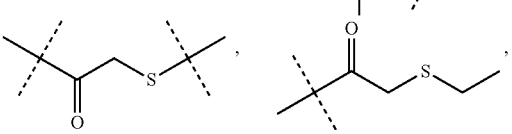
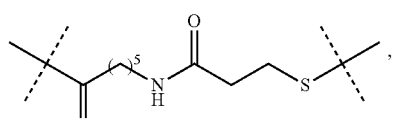
and
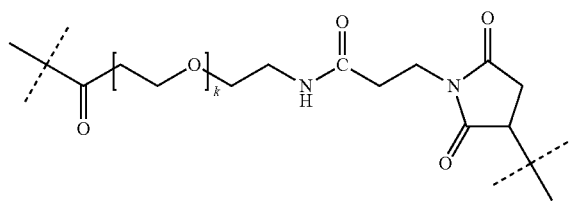
when Z represents a maleimide group or a halogen atom.
In a preferred embodiment, the linker will be chosen among:
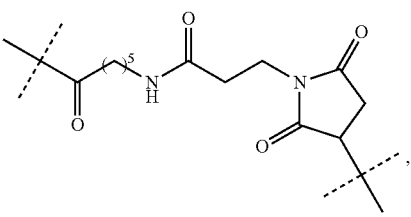
with k representing an integer comprised between 2 and 24, and being advantageously 2, 4, 8 or 12 and with k1 representing an integer comprised between 1 and 10, thus equal to 1, 2, 3, 4, 5, 6, 7, 8, 9 or 10, and advantageously equal to 1, 2, 3, 5 or 10,
when Z represents a thiol group,
and among:

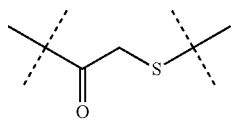

and

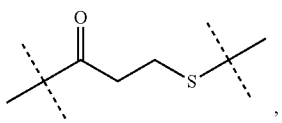

, when Z represents a maleimide group or a halogen atom.

Such linkers correspond thus to the use of succinimidyl-6-[beta-maleimidopropionamido] hexanoate (SMPH), NHS-PEO$_n$-maleimide, with n representing an integer comprised between 2 and 24, and being advantageously 2, 4, 8 or 12, SATA (N-succinimidyl-S-acetylthioacetate) and SATP (N-succinimidyl-S-acetylthiopropionate), as bifunctional compound.

In another preferred embodiment, the linker is:

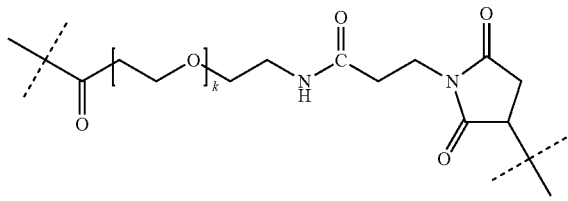

with k representing an integer comprised between 2 and 24, and being advantageously 2, 4, 8 or 12 and
advantageously is:

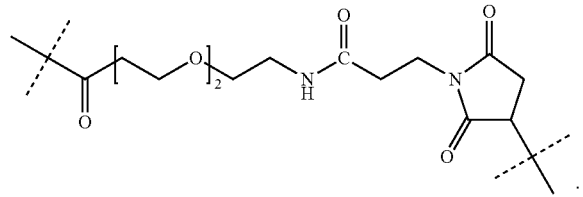

The conjugated molecule of the invention comprises an anionic polypeptide, said anionic peptide consisting of 5 to 21, notably 10 to 17, preferably 13 amino acids, wherein 3, 4, 5, 6, 7, 8, 9, 10, 11, 12 or 13 amino acid residues are negatively charged. In a preferred embodiment, the anionic polypeptide consists of 13 amino acids, wherein 9 amino acid residues are negatively charged.

The anionic polypeptide of the invention is linked to the A group by its N-terminal end. The bond formed between the said anionic peptide and the A group is a peptidic bond (NH—CO), wherein the NH part of the peptidic bond corresponds to the terminal amino group (NH$_2$) of the said anionic peptide and the CO part of the peptidic bond corresponds to the first carboxylic group of the A group.

Without being bound by any theory, it is thought that the said anionic polypeptides impair the interaction between the CD4i exposed site and CXCR4 (or CCR5) chemokine receptors, thereby impairing the initiation of the cell/virus membrane fusion.

In the sense of the present invention, "amino acids" means all natural α-amino acid residues (for example alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophane (Trp), tyrosine (Tyr) and valine (Val)) in D or L form, as well as non-natural amino acids (for example, β-alanine, allylglycine, tert-leucine, norleucine (NLe), 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxylic acid, (1R,2R)-2-aminocyclohexanecarboxylic acid, (1R,2S)-2-aminocyclohexanecarboxylic acid, (1 S,2R)-2-aminocyclohexanecarboxylic acid, (1 S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (LR,2S)-2-aminocyclopentanecarboxylic acid 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methytheptanoic acid, (R)-4-amino-5-methythexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S, 4R)-4-amino-pyrrotidine-2-carboxylic acid, (2S,4S)-4-amino-pyrrotidine-2-carboxylic acid, azetidine-2-carboxylic acid, (2S,4R)-4-benzyl-pyrrotidine-2-carboxylic acid, (S)-4, 8-diaminooctanoic acid, tert-butylglycine, γ-carboxyglutamate, β-cyclohexylalanine, citruline, 2,3-diamino propionic acid, hippuric acid, homocyclohexylalanine, moleucine, homophenylalanine, 4-hydroxyproline, indoline-2-carboxylic acid, isonipecotic acid, sulfotyrosine, aminosuberic acid, p-carboxymethyl phenylalanine, α-methyl-alanine, nicopetic acid, norvaline, octahydroindole-2-carboxylic acid, ornithine, penicillamine, phenylglycine (Phg), 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, the statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4,4',4',4'-hexafluorovaline, pentafluorophenylalanine, 2,3-difluorophenylalanine, 2,4-difluorophenylalanine, 2,5-difluorophenylalanine, 2,6-difluorophenylalanine, 3,4-difluorophenylalanine, 3,5- difluorophenylalanine, 3,3-difluoro-3-(4-fluorophenyl) alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine and hexafluoronorleucine). The term also includes natural and non-natural amino acids carrying a conventional amino protecting group (for example, an acetyl group, tert-butyloxycarbonyl, benzyloxycarbonyl or 9-fluorenylmethylcarbonyl), as well as natural and non-natural amino acids protected at the carboxylic end (advantageously by a $C_1$-$C_{18}$ alkyl group, an ester, a phenyl amide or benzyl amide or an amide, which, respectively, give a carboxylic end of the following formula: —CO($C_1$-$C_{18}$ alkyl), —COO($C_1$-$C_{18}$ alkyl), CONHphenyl, CONHbenzyl, or $CONH_2$).

As used herein, the term "anionic" designates a negatively charged molecule, which for example migrates to an anode in electrolysis. Also, a "negatively charged" amino acid designates an amino acid which carries a side-chain charge which is negative at a pH of 7.4. Negatively charged amino acid residues according to the invention thus include, for example, aspartic acid, sulfotyrosine, tyrosine sulfonate, aminosuberic acid, p-carboxymethyl phenylalanine, and glutamic acid residues.

As used herein, sulfotyrosine (or 2-amino-3-(4-(sulfooxy) phenyl) propanoic acid) is a non-natural amino acid having the following formula:

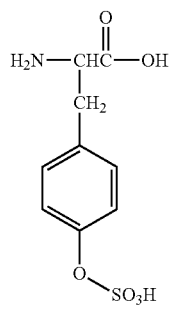

As used herein, the term "tyrosine sulfonate" (or "2-amino-3-(4-(sulfomethyl)phenyl) propanoic acid") refers to a non-natural amino acid having the following formula:

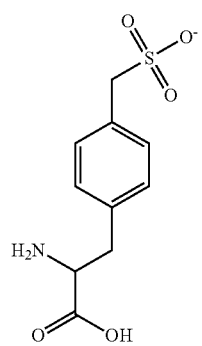

According to the present invention, aminosuberic acid is a non-natural amino acid having the following formula:

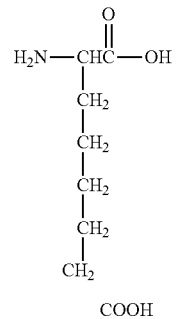

As used herein, p-carboxymethyl phenylalanine refers to a non-natural amino acid having the following formula:

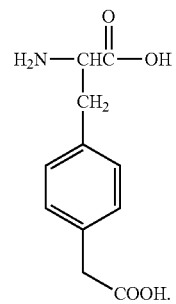

In one embodiment of the invention, the said anionic polypeptide consists of 13 identical negatively charged amino acids. It can be, for example, the polypeptide consisting of 13 aspartic acid residues (SEQ ID NO: 9), 13 sulfotyrosine residues (SEQ ID NO: 10), 13 tyrosine sulfonate residues (SEQ ID NO: 11), 13 aminosuberic acid residues (SEQ ID NO: 12), 13 p-carboxymethyl phenylalanine residues (SEQ ID NO: 13), or 13 glutamic acid residues (SEQ ID NO: 3). In a preferred embodiment, said identical amino acid is glutamic acid E and the anionic polypeptide of the conjugated molecule of the invention is SEQ ID NO: 3.

In another embodiment of the invention, the anionic peptide of the invention comprises negatively charged and uncharged amino acids. Preferably, the said anionic peptide comprises at least one negatively charged amino acid and at least another amino acid. Preferably, the said other amino acid is an amino acid carrying a polar uncharged side chain. Such amino acids include e.g. serine, threonine, asparagine, and glutamine. In a further preferred embodiment, the said other amino acid is serine or threonine. In a still further preferred embodiment, the said other amino acid is serine. In another preferred embodiment, the negatively charged amino acid is aspartic acid.

In another further preferred embodiment, the said anionic polypeptide of the invention comprises at least two different negatively charged amino acids, in addition to the at least one other amino acid. In this case, said anionic polypeptide has for example the sequence S-(X-D-X-S)$_n$, such as S-X-D-X-S-X-D-X-S-X-D-X-S(SEQ ID NO: 19), where n is an integer comprised between 1 and 5, and preferably is 3, S represents serine, D represents aspartic acid, and X is selected from the group consisting of: tyrosine, sulfotyrosine, tyrosine sulfonate, aminosuberic acid, and p-carboxymethyl phenylalanine and where the various X groups can be identical or different, preferably identical.

In this embodiment, said anionic polypeptide can have in particular any of the following sequences:

S-(Y$_{SO3}$-D-Y$_{SO3}$-S)$_n$, such as S-Y$_{SO3}$-D-Y$_{SO3}$-S-Y$_{SO3}$-D-Y$_{SO3}$-S-Y$_{SO3}$-D-Y$_{SO3}$-S(SEQ ID NO: 4), where Y$_{SO3}$ is sulfotyrosine;

S-(Y$_{SN}$-D-Y$_{SN}$-S)$_n$, such as S-Y$_{SN}$-D-Y$_{SN}$-S-Y$_{SN}$-D-Y$_{SN}$-S-Y$_{SN}$-D-Y$_{SN}$-S(SEQ ID NO: 5), where Y$_{SN}$ is tyrosine sulfonate;

S-(pF-D-pF-S)$_n$, such as S-pF-D-pF-S-pF-D-pF-S-pF-D-pF-S(SEQ ID NO: 6), where pF is p-carboxymethyl phenylalanine;

S-(Asu-D-Asu-S)$_n$, such as S-Asu-D-Asu-S-Asu-D-Asu-S-Asu-D-Asu-S(SEQ ID NO: 7), where Asu is aminosuberic acid; and S-(Y-D-Y-S)$_n$, such as S-Y-D-Y-S-Y-D-Y-S-Y-D-Y-S (SEQ ID NO: 8), where Y is tyrosine.

The anionic polypeptide can have also the following sequences:

S-Y$_{SO3}$-D-Y$_{SO3}$-S-Y$_{SO3}$-D-Y-S-Y-D-Y-S(SEQ ID NO: 14), or

S-Y-D-Y—S-Y-D-Y$_{SO3}$-S-Y$_{SO3}$-D-Y$_{SO3}$-S(SEQ ID NO: 15).

Most preferably according to the invention, X represents sulfotyrosine. Therefore, in the most preferred embodiment, the anionic polypeptide of the invention has the sequence: S-(Y$_{SO3}$-D-Y$_{SO3}$-S)$_n$, and in particular S-Y$_{SO3}$-D-Y$_{SO3}$-S-Y$_{SO3}$-D-Y$_{SO3}$-S-Y$_{SO3}$-D-Y$_{SO3}$-S(SEQ ID NO: 4).

In a particular embodiment, the conjugated molecule of the invention comprises a peptide derived from the CD4 receptor, said peptide being coupled to an organic molecule by means of a linker, wherein:
the peptide derived from the CD4 receptor is chosen from the group consisting of sequences SEQ ID NO: 1, SEQ ID NO: 2, SEQ ID NO: 20 and SEQ ID NO: 21, preferably chosen from the group consisting of sequences SEQ ID NO: 1 and SEQ ID NO: 1,
the linker is CO—(CH$_2$CH$_2$O)$_2$CH$_2$CH$_2$NHCO(CH$_2$)$_2$-pyrrolidinyl-2,5-dione,
the organic molecule comprises an anionic polypeptide having a sequence selected from the group consisting of: S-(Y$_{SO3}$-D-Y$_{SO3}$-S)$_n$, S-(Y$_{SN}$-D-Y$_{SN}$-S)$_n$, S-(pF-D-pF-S)$_n$, S-(Asu-D-Asu-S)$_n$, and S-(Y-D-Y-S)$_n$; and in particular selected from the group consisting of: S-Y$_{SO3}$-D-Y$_{SO3}$-S-Y$_{SO3}$-D-Y$_{SO3}$-S-Y$_{SO3}$-D-Y$_{SO3}$-S (SEQ ID NO 4), S-Y$_{SN}$-D-Y$_{SN}$-S-Y$_{SN}$-D-Y$_{SN}$-S-Y$_{SN}$-D-Y$_{SN}$-S(SEQ ID NO: 5), S-pF-D-pF-S-pF-D-pF-S-pF-D-pF-S(SEQ ID NO: 6), S-Asu-D-Asu-S-Asu-D-Asu-S-Asu-D-Asu-S(SEQ ID NO: 7), S-Y-D-Y-S-Y-D-Y-S-Y-D-Y-S (SEQ ID NO: 8), said sequence being linked to the linker by a molecular group of formula A-Z, wherein A is —CO(CH$_2$)$_3$NH—CO(CH$_2$)$_2$— and Z is a thiol group.

In a preferred embodiment, the conjugated molecule of the invention comprises the peptide derived from the CD4 receptor chosen from the group consisting of sequences SEQ ID NO: 1, SEQ ID NO: 2, SEQ ID NO: 20 and SEQ ID NO: 21, preferably chosen from the group consisting of sequences SEQ ID NO: 1 and SEQ ID NO: 2, and advantageously having the sequence SEQ ID NO: 1, said peptide being coupled to an organic molecule by means of the linker CO—(CH$_2$CH$_2$O)$_2$CH$_2$CH$_2$NHCO(CH$_2$)$_2$-pyrrolidinyl-2,5-dione, and an anionic polypeptide having the sequence S-(Y$_{SO3}$-D-Y$_{SO3}$-S)$_n$, and in particular S-Y$_{SO3}$-D-Y$_{SO3}$-S-Y$_{SO3}$-D-Y$_{SO3}$-S-Y$_{SO3}$-D-Y$_{SO3}$-S(SEQ ID NO 4), said sequence being linked to the linker by a molecular group of formula A-Z, wherein A is —CO(CH$_2$)$_3$NH—CO(CH$_2$)$_2$— and Z is a thiol group.

The conjugated molecules of the invention are capable of inhibiting HIV entry into the cell, by blocking the attachment of the virus on the cell membrane and thereby the virus entry. The conjugated molecules of the invention can therefore be used in therapy. More preferably, the conjugated molecules of the invention can be used for treating viral infections. Even more preferably, the said conjugated molecules can be used for treating AIDS. Therefore, according to a second aspect, the invention covers a conjugated molecule as defined above for its use as medicament. The invention also relates to the conjugated molecules as defined above for treating viral infections, and, in particular, for the treatment of AIDS. The use of a conjugated molecule as defined above for the manufacture of a medicament, in particular for an antiviral treatment, such as for the treatment of AIDS, is also an object of the present invention.

According to a third aspect, the invention covers a pharmaceutical composition comprising a conjugated molecule as defined above and a pharmaceutically acceptable vehicle. This composition can be used as a medicament, preferably for the treatment of viral infections, and, more preferably, for the treatment of AIDS.

In the pharmaceutical compositions of the present invention for oral, intranasal, sublingual, subcutaneous, intramuscular, intravenous, transdermal, local, vaginal or rectal administration, the active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

The pharmaceutical composition of the invention may contain, in addition to the carrier and conjugated molecule of the invention, various diluents, fillers, salts, buffers, stabilizers, solubilizers, and other materials well known in the art.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof, which are incorporated herein by reference.

The conjugated molecule in the composition preferably is formulated in an effective amount. An "effective amount" refers to an amount effective, at dosages and for periods of time necessary, to achieve the desired result, such as partial or total inhibition of viral infection. A "therapeutically effective amount" means an amount sufficient to influence the therapeutic course of a particular disease state. A therapeutically effective amount is also one in which any toxic or detrimental effects of the agent are outweighed by the therapeutically beneficial effects.

Dosage regimens may be adjusted to provide the optimum response. For example, a single bolus may be administered, several divided doses may be administered over time, or the dose may be proportionally reduced or increased. The compositions of the invention can be administered to a subject to affect viral infection in a subject. As used herein, the term "subject" is intended to include living organisms which is susceptible to viral infection, and specifically includes mammals, such as rabbits, dogs, cats, mice, rats, monkey transgenic species thereof, and preferably humans.

For therapeutic applications, the conjugated molecule of the invention is administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerebrospinal, subcutaneous, intraarticular, intrasynovial, intrathecal, oral, topical, or inhalation routes.

The invention also relates to an antiviral treatment method, preferably an anti-AIDS treatment method, comprising the administration to a subject in need thereof of an effective amount of a conjugated molecule according to the invention or a pharmaceutical composition containing it as defined above.

In a fourth aspect, the invention provides a process for the preparation of a conjugated molecule as defined above, characterized in that the process comprises the following steps:
  a. contacting the miniCD4 peptide of general sequence (I) as defined above with a bifunctional compound carrying two active groups, so that one of the two active groups forms a covalent bond with the free amino group (—NH$_2$) of the residue of the amino acid Lys present in general sequence (I), in order to obtain an activated peptide carrying the second active group of the bifunctional group, and
  b. contacting the activated peptide obtained at step (a) with an organic molecule as defined above, wherein Z can be in a protected form when Z is a thiol group, so that the active group of the activated peptide reacts with the Z group of the organic molecule to form a covalent bond between the organic molecule and the activated peptide, in order to obtain the conjugated molecule.

The compound obtained at step (a) will be called indifferently, in the present application, "activated peptide", "activated miniCD4", "activated CD4 peptide" or "activated miniCD4 peptide".

The active groups of the bifunctional compound can be, independently of each other, a halogen atom, a maleimide, a thiol or a protected thiol group.

When the thiol group is in a protected form, it means that the thiol function is substituted by a S-protecting group in order to protect the thiol group against undesirable reactions during synthetic procedures. Commonly used S-protecting groups are disclosed in Greene, "Protective Groups In Organic Synthesis," (John Wiley & Sons, New York (1981)). The protected thiol group can be benzyl thioethers, substituted or not, such as p-methoxybenzyl and p-nitrobenzyl thioethers, trityl thioethers, thioethers, thioacetate or thioacetal. Advantageously, the protected thiol group is a thioacetyl group.

When the organic compound or the activated peptide carries a protected thiol group, said protected group will be deprotected before or during step (b), in order to recover a free thiol group and to allow the coupling of this thiol with the active group of the activated peptide or with the Z group of the organic compound respectively.

When the thiol group is protected in the form of a thioacetyl group, hydroxylamine can be used for example to deprotect the thiol group. This step can be carried out simultaneously to a coupling to a maleimide group (active group of the activated peptide or Z group of the organic compound).

The characteristics of the peptide derived from CD4 receptor are the same as defined above. In particular, P3 comprises preferably at least one basic amino acid, said basic amino acid being even more preferably arginine. According to a preferred embodiment, Xaa$^f$ represents TPA in general sequence (I). According to another preferred embodiment, Xaa$^j$ represents U$_1$. Preferably, the sequence of the peptide derived from the CD4 receptor of general sequence (I) is chosen from the group consisting of sequences SEQ ID NO: 1, SEQ ID NO: 2, SEQ ID NO: 20 and SEQ ID NO: 21, preferably chosen from the group consisting of sequences SEQ ID NO: 1 and SEQ ID NO: 2, and is advantageously SEQ ID NO: 1.

The term "bifunctional compound" in this patent application refers to any compound incorporating two active groups wherein one of the two active groups is capable of forming a covalent bond with the free amino group (—NH$_2$) of the residue of the amino acid Lys present in general sequence (I) and the other active group is capable of forming a covalent bond with the organic molecule.

The person skilled in the art knows well the bifunctional compounds which can be used within the framework of this invention. Namely, the bifunctional compound according to this invention can be chosen from the following non-limiting list: NHS-PEO$_n$-Maleimide where n is comprised between 2 and 24, advantageously n=2, 4, 8 or 12, Sulfo-KMUS (N-[k-maleimidoundecanoyloxy] sulfosuccinimide ester), LC-SMCC (succinimidyl-4-[N-maleimidomethyl]cyclohexane-1-carboxy-[6-amidocaproate]), KMUA (N-k-maleimidoundecanoic acid), SMPB (succinimidyl 4-[p-maleimidophenyl]butyrate), Sulfo-SMPB (sulfosuccinimidyl 4-[p-maleimidophenyl]butyrate), Sulfo-SIAB (N-sulfosuccinimidyl[4-iodoacetyl]aminobenzoate), SIAB (N-succinimidyl[4-iodoacetyl]aminobenzoate), Sulfo-EMCS ([N-e-maleimidocaproyloxy]sulfosuccinimide ester), EMCA (N-e-maleimidocaproic acid), EMCS ([N-e-maleimidocaproyloxy]succinimide ester), SMCC (succinimidyl 4-[N-maleimidomethyl]cyclohexane-1-carboxylate), Sulfo-SMCC (sulfosuccinimidyl 4-[N-maleimidomethyl]cyclohexane-1-carboxylate), MBS (m-maleimidobenzoyl-N-hydroxy succinimide ester), Sulfo-MBS (m-maleimidobenzoyl-N-hydroxysulfosuccinimide ester), GMBS (N-[g-maleimidobutyryloxy]succinimide ester), Sulfo-GMBS (N-[g-maleimidobutyryloxy]sulfosuccinimide ester), SPDP (N-succinimidyl-3-(2-pyridyldithio)propionate), SBAP (succinimidyl 3-[bromoacetamido]propionate), BMPS (N-[[beta]-maleimidopropyloxy]succinimide ester), BMPA (N-[beta]-maleimidopropionic acid), AMAS N-(a-maleimidoacetoxy) succinimide ester), SIA (N-succinimidyl iodoacetate), SMPH(succinimidyl-6-[betamaleimidopropionamido]hexanoate), SATA (N-succinimidyl-S-acetylthioacetate) and SATP (N-succinimidyl-S-acetylthiopropionate).

According to the invention, NHS-PEO$_n$-Maleimide wherein n=2 is also called succinimidyl-[(N-maleimidoproprionamido)-diethyleneglycol]ester, NHS-PEO$_n$-Maleimide wherein n=4 is also called succinimidyl-[(N-maleimidoproprionamido)-tetraethylenegtycot]ester, NHS-PEO$_n$-Maleimide wherein n=8 is also called succinimidyl-[(N-maleimidoproprionamido)-octaethyleneglycol]ester, NHS-PEO$_n$-Maleimide wherein n=12 is also called succinimidyl-[(N-maleimidoproprionamido)-dodecaethyleneglycol]ester.

The active group capable of forming a covalent bond with the free amine group (—NH$_2$) of the residue of amino acid Lys present in general sequence (I) can be any active ester group.

Preferably, the active group capable of forming a covalent bond with the free amine group (—NH$_2$) of the residue of amino acid Lys present in general sequence (I) is the active group N-hydroxysuccinimide ester (NHS) or N-hydroxy-4-sulfo-succinimide ester, and advantageously is the NHS active group. Even more preferably, the two active groups of the bifunctional compound are different (heterobifunctional compound) and one of the two groups is the NHS active group or a N-hydroxy-4-sulfo-succinimide ester, and advantageously is the NHS active group.

Advantageously, the active group of the bifunctional compound, capable of forming a covalent group with the organic molecule, is a halogen atom or a maleimide group when the functional group of the organic molecule is a thiol or a protected thiol group and is a thiol or a protected thiol group, as defined above, when the functional group of the organic molecule is a halogen atom or a maleimide group.

According to a preferred embodiment, when the functional group of the organic molecule is a thiol group or a protected thiol group, the bifunctional compound is chosen from the group consisting of succinimidyl-6-[beta-maleimidopropionamido]hexanoate (SMPH) and NHS-PEO$_n$-maleimide, n being comprised between 2 and 24, and advantageously is 2, 4, 8 or 12.

According to a particularly preferred embodiment, the bifunctional compound is SMPH.

The molecular structure of SMPH is as follows:

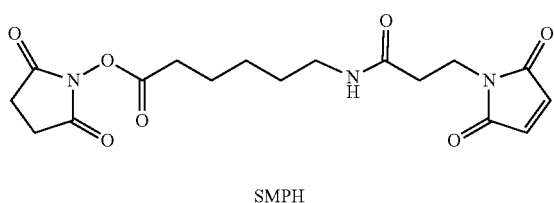

SMPH

According to yet another particularly preferred embodiment, the bifunctional compound is succinimidyl-[(N-maleimidopropionamido)-diethyleneglycol] ester, also called NHS-PEO$_2$-maleimide, succinimidyl-[(N-maleimidopropionamido)-tetraethyleneglycol] ester, also called NHS-PEO$_4$-maleimide, succinimidyl-[(N-maleimidopropionamido)-octaethyleneglycol] ester, also called NHS-PEO$_8$-maleimide, succinimidyl-[(N-maleimidopropionamido)-dodecaethyleneglycol] ester, also called NHS-PEO$_{12}$-maleimide, still more preferably the bifunctional compound is NHS-PEO$_2$-maleimide.

The molecular structure of NHS-PEO$_2$-maleimide is as follows:

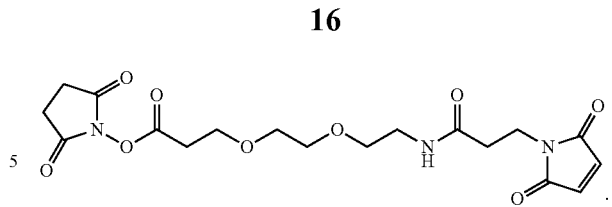

According to another particularly preferred embodiment, when the functional group of the organic molecule is a halogen atom or a maleimide group, the bifunctional compound is chosen from the group consisting of N-succinimidyl-S-acetylthioacetate (SATA) and N-succinimidyl-S-acetylthiopropionate (SATP).

The molecular structure of SATA is as follows:

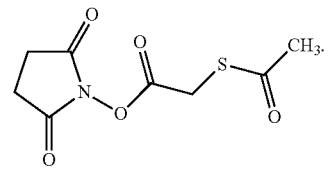 [SMILES: CC(=O)SCC(=O)ON1C(=O)CCC1=O]

The molecular structure of SATP is as follows:

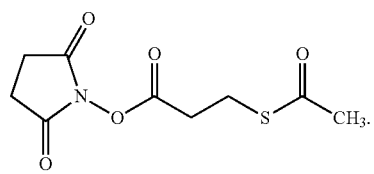 [SMILES: CC(=O)SCCC(=O)ON1C(=O)CCC1=O]

The bifunctional compounds can be obtained from PIERCE (Rockford, Ill.).

Preferably again, the process according to the invention includes a preliminary step for the preparation of the peptide derived from the CD4 receptor of general sequence (I), when Xaa$^f$ represents TPA, said step consisting of contacting the peptide derived from the CD4 receptor of the following general sequence (II):

P1-Lys-Cys-P2-Cys-P3-Cys-Xaa$^g$-Xaa$^h$-Xaa$^i$-Xaa$^j$-Cys-Xaa$^k$-Cys-Xaa$^l$-Xaa$^m$, (II)

where P1 to P3 and Xaa$^g$ to Xaa$^m$ are as defined in general sequence (I), with N-succinimidyl-3-(2-pyridyldithio)propionate (SPDP) in order to incorporate TPA at the N-terminus of said peptide derived from the CD4 receptor of general sequence (II).

The molecular structure of SPDP is as follows:

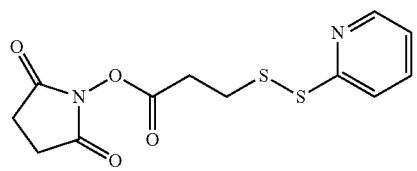

Moreover, as examples of active groups capable of coupling to the organic molecule by means of a covalent bond, the following groups can be cited: maleimide or bromoacetyl, S—S-pyridinium or thioacetyl.

Preferably, the active group capable of coupling to the organic molecule is the maleimide group.

When activated miniCD4 carries as active group a maleimide group, it is possible to carry out the coupling to an organic molecule which carries a thiol group or a protected thiol group. If the thiol group is in a protected form, it has to be deprotected to allow the coupling reaction with the maleimide group of the activated miniCD4.

The molecular structure of the activated peptide according to the invention whose active group is maleimide is the following when SMPH is the bifunctional compound used:

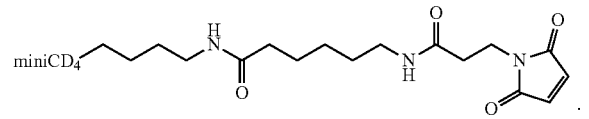

In this application, the term "SMPH activated miniCD4 peptide" refers to an activated peptide according to the invention whose amino acid Lys residue is covalently bound, advantageously by an amine bond, to a maleimide active group via a linker derived from SMPH.

According to another advantageous embodiment, the molecular structure of the activated peptide according to the invention whose active group is the maleimide group is the following when NHS-PEO$_2$-maleimide is the bifunctional compound used:

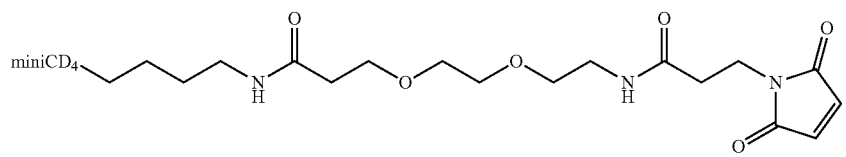

In this application, the term "maleimide activated miniCD4 peptide via a PEO$_2$ linker" refers to an activated peptide according to the invention whose amino acid Lys residue is covalently bound, advantageously by an amine bond, to a maleimide active group via a PEO$_2$ linker.

According to another preference, the active group capable of coupling to the organic molecule is the thioacetyl group.

When activated miniCD4 carries as active group a thiol group or a protected thiol group (e.g. thioacetyl), it is possible to carry out the coupling to an organic molecule which carries a maleimide group for example. This is possible when the functionalisation of the polyanionic polypeptide by a thiol group or protected thiol group, such as thioacetyl, poses a problem. This then called "reverse coupling". If the thiol group carried by the activated miniCD4 is in a protected form, it has to be deprotected to allow the coupling reaction with the maleimide group carried by the organic molecule.

For example, the molecular structure of the activated peptide according to this invention whose active group is the thioacetyl group is the following when SATA is the bifunctional compound used:

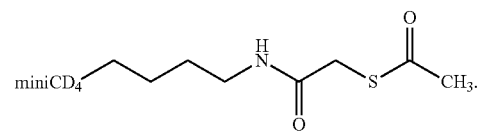

Similarly, the molecular structure of the activated peptide according to this invention whose active group is the thioacetyl group is the following when SATP is the bifunctional compound used:

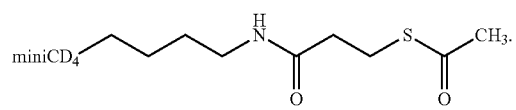

In this application, the terms "SATA activated miniCD4 peptide" and "SATP activated miniCD4 peptide" refer to an activated peptide according to the invention whose amino acid Lys residue is covalently bound, advantageously by an amine bond, to a protected thiol group (e.g. thioacetyl) via a linker derived from SATA or SATP.

Thus, according to a particular embodiment, the active group of the activated peptide is the maleimide group and the organic molecule carries a thiol or thioacetyl group.

The molecular structure of a conjugated molecule according to the invention, including a peptide derived from the CD4 receptor of general sequence (I) coupled to a modified anionic polypeptide (polyanion) carrying a thiol or protected thiol group, such as a thioacetyl group, is as follows when SMPH was used as bifunctional compound for the coupling:

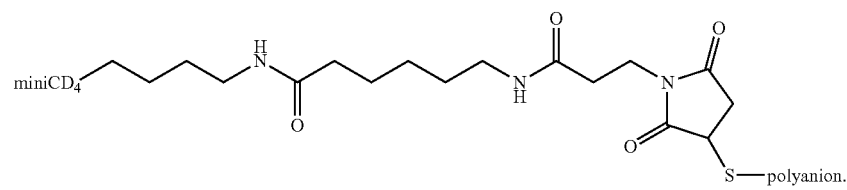

It can also be the following conjugated molecule when NHS-PEO$_2$-maleimide is the bifunctional compound used:

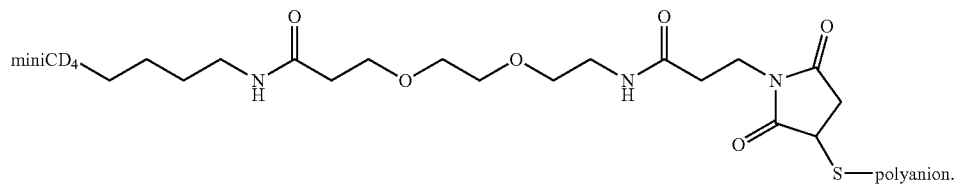

According to another embodiment, the conjugated molecule according to the invention comprises a peptide derived from the CD4 receptor comprising or consisting of general sequence (I), advantageously sequence SEQ ID NO: 1, SEQ ID NO: 2, SEQ ID NO: 20 or SEQ ID NO: 21, preferably sequence SEQ ID NO: 1 or SEQ ID NO: 2, and an organic molecule carrying a maleimide or halogen group.

According to another particular embodiment, the active group of the activated peptide is the thioacetyl group and the organic molecule carries a maleimide or halogen group.

For example, the molecular structure of such a conjugated molecule including a peptide derived from the CD4 receptor of general sequence (I) coupled to an organic molecule carrying a maleimide group is as follows when SATA is used for the coupling:

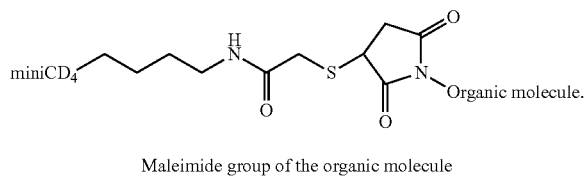

Maleimide group of the organic molecule

According to the invention, the anionic polypeptide can be prepared by any convenient synthetic method known in the art. The operating conditions for the processes according to the invention for preparation of the activated peptide and conjugated molecule are well known to the person skilled in the art as illustrated in the following examples.

The examples and figures below illustrate the invention but do not limit its scope in any way.

FIGURES

EXPERIMENTAL EXAMPLES

Material and Methods

Reagents

Figure 1:
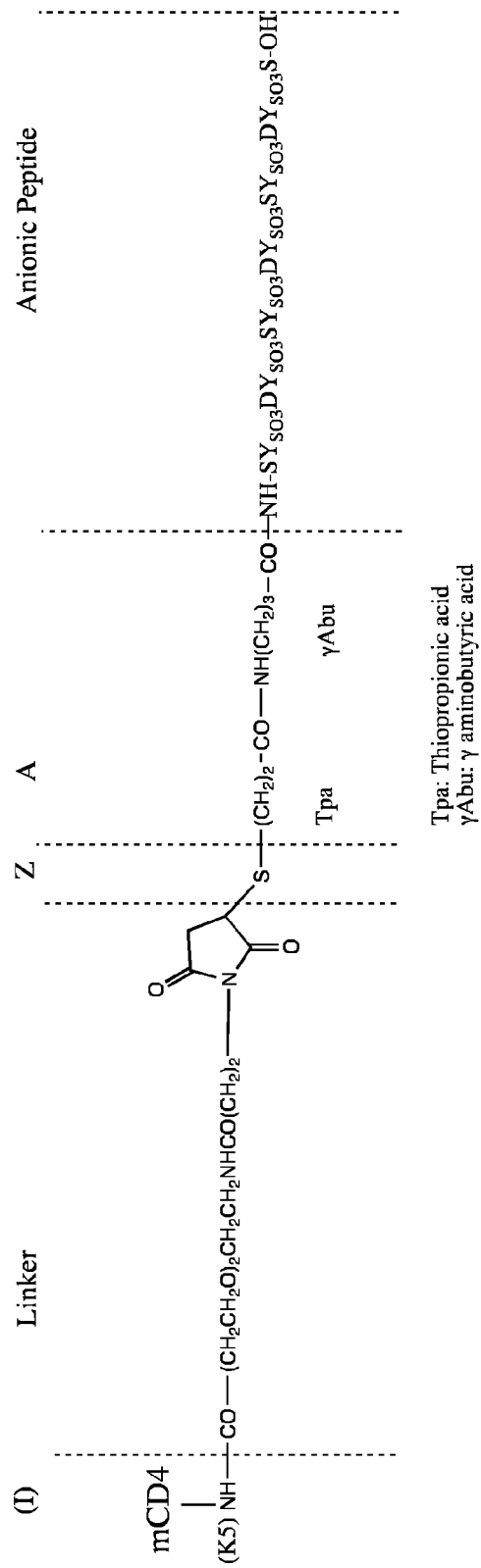
FIG. 1 represents the structure of the conjugated molecules of the invention.
Figure 2:
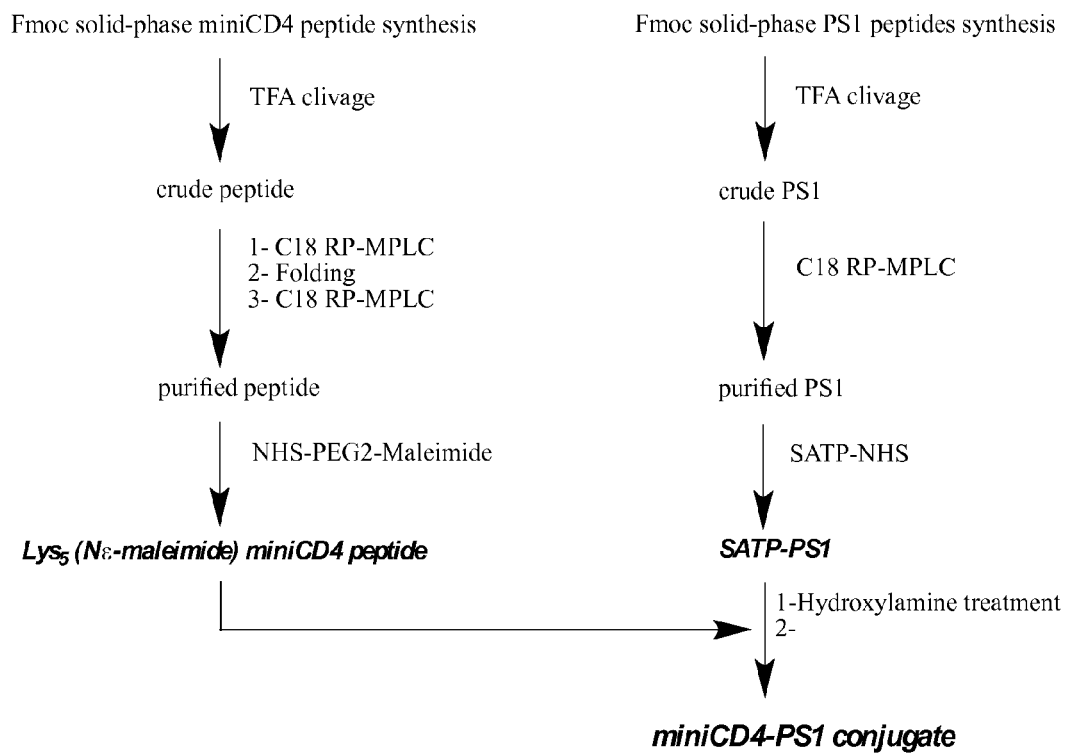
FIG. 2 represents the synthesis scheme of the conjugated molecules of the invention.

All reagents for peptides synthesis were from Applied Biosystems/Life Technolgies, except Fmoc-4,4'-Biphenylalanine (Fmoc-Bip) from Interchim, S-trityl Thiopropionic acid (S-trityl Tpa) and Fmoc-4-cyclohexylmethoxy-L-phenylalanine (Fmoc-$U_1$) from Iris Biotech GmbH, Fmoc-γAminobutyric acid (Fmoc-γAbu), Fmoc-D-Proline and Fmoc-L-O-sulfo-Tyrosine tetrabutylammonium salt, pseudoproline dipeptides Fmoc-Ser(tBu)-Ser($\Psi^{Me,Me}$Pro) and Fmoc-Gly-Ser($\Psi^{Me,Me}$Pro) from Novabiochem. Succinimidyl-[(N-maleimidopropionamido)-diethyleneglycol] ester (NHS-$PEG_2$-Maleimide) and SATP-NHS (N-Succinimidyl S-Acetylthiopropionate) were from Pierce/Thermo Scientific. PS 2-CT-Ser (tBu) was from Rapp polymere GmbH.

All peptides and conjugates were controlled by HPLC, mass spectrometry (ESI-MS on Q-Tof micro Waters). Synthesis yields were calculated after quantification by amino acids analysis on a Hitachi L8800 apparatus.

General Protocol for miniCD4 Peptides Synthesis

MiniCD4 peptides were synthesized on a Rink Amide resin (100 μmoles) using Fmoc chemistry and HATU/DIEA activation for Fmoc amino acids coupling on an AB1433 apparatus. For mCD4.1, Ser11Ser12 and GLy21Ser22 were introduced as pseudoproline dipeptides. After chain elongation, peptides were released from the resin by TFA/$H_2O$/Thioanisole/Phenol/Ethanedithiol/Triisopropyl silane (82/5/5/5/2/1), 20 ml, 4° C., 2 h30 treatment. Precipitation in cold diethylether afforded the crude peptides that were collected by centrifugation then solubilized in Aqueous 0.08% TFA/acetonitrile and freeze-dried. Crude peptides were purified by C18 Reverse-Phase Medium Pressure Chromatography (C18 RP-MPLC, 30 mm×340 mm column) using a 20-60 linear gradient of acetonitrile in 0.08% aqueous TFA over 60 minutes at 25 ml flow rate. Purified SH peptides (130 mg) were dissolved in 65 ml of water then dilute with 65 ml of 0.1 M pH8.5 TRIS buffer. Folding was performed by sequential addition of 796 mg of GSH and 158 mg of GSSG (20 mM/2 mM final concentration). Folding was followed by analytical RP-HPLC and was complete after 45 minutes. After acidification of the reaction mixture by 1 ml of pure AcOH, folded mini CD4 peptides were isolated by RP-MPLC using a 0-60 linear gradient with the same eluents as above. MiniCD4 peptides were controlled by MS using positive mode.

| Sequence | Peptide | Yield (%) | Formula | MS expected [M + H]⁺ | MS found [M + H]⁺ |
|---|---|---|---|---|---|
| SEQ ID NO: 16 | mCD4.1* | 21 | $C_{122}H_{194}N_{38}O_{32}S_6$ | 2896.3124 | 2896.4170 |
| SEQ ID NO: 17 | M48U1* | 6 | $C_{133}H_{212}N_{38}O_{32}S_6$ | 3046.4532 | 3046.4294 |
| SEQ ID NO: 1 | mCD4.2 | 15 | $C_{127}H_{208}N_{38}O_{33}S_6$ | 2986.4169 | 2986.4021 |
| SEQ ID NO: 2 | mCD4.3 | 21 | $C_{130}H_{215}N_{41}O_{32}S_6$ | 3055.4259 | 3055.4546 |

*reference peptides

General Protocol for Activated miniCD4 Peptides Synthesis (Lys5/11 (NE-Maleimide) miniCD4 Peptides)

To 51 mg of miniCD4 peptide in 26 ml of water was slowly added 3 ml of 0.1 M sodium phosphate buffer pH7.2 under mild agitation to avoid foaming. NHS-PEG2-Maleimide (75 mgs, 10 molar equivalents) in 750 µl of DMSO was dropwise added to the peptide solution. After 10 minutes, the reaction mixture was acidified by 1.2 ml of pure AcOH and purified by C18 RP-MPLC using the same conditions as for miniCD4 peptide. Activated miniCD4 peptides were controlled by MS using positive mode.

| Activated peptide | Yield (%) | Formula | MS expected [M + H]⁺ | MS found [M + H]⁺ |
|---|---|---|---|---|
| mCD4.1Mal* | 77 | $C_{136}H_{212}N_{40}O_{38}S_6$ | 3206.4289 | 3206.6572 |
| M48U1Mal* | 80 | $C_{147}H_{230}N_{40}O_{38}S_6$ | 3356.5697 | 3356.4619 |
| mCD4.2Mal | 60 | $C_{141}H_{226}N_{40}O_{39}S_6$ | 3296.5333 | 3296.4609 |
| mCD4.3Mal | 66 | $C_{144}H_{233}N_{43}O_{38}S_6$ | 3365.6024 | 3365.7483 |

*reference activated peptides

Protocol for Anionic Polypeptide (γAbu-PSI) Synthesis

PS1 peptide (SEQ ID NO: 4) was synthesized on a Serine preloaded Chlorotrityl resin, PS 2-CT-Ser (tBu), (100 µmoles). Tyrosine sulfate was incorporated using Fmoc-L-O-sulfo-Tyrosine tetrabutylammonium salt. γAminobutyric acid was introduced at the N-terminus of the peptide chain using standard amino acid coupling protocol. In order to maintain the sulfate group on the tyrosine residues, all the cleavage protocol was performed at 4° C. (ice bath). After 1 h30 in TFA/TIS/H₂O 95/2.5/2.5 (9 ml), precipitation in cold diethylether afforded the crude peptide that was collected by centrifugation, solubilized in 30 ml of 100 mM ammonium hydrogenocarbonate and freeze-dried. Crude peptide was purified by C18 RP-MPLC using a 0-60 linear gradient of acetonitrile in 0.1 M Triethylacetate buffer over 60 minutes. γAbu-PS1 was controlled by MS using negative mode.

| Sequence | Polyanionic peptide | Yield (%) | Formula | MS expected [M − H]⁻ | MS found [M − H]⁻ |
|---|---|---|---|---|---|
| SEQ ID NO: 18 | γAbu-PS1 | 37 | $C_{82}H_{98}N_{14}O_{49}S_6$ | 2253.3811 | 2253.3853 |

Protocol for SATP-γAbu-PS1 Peptide Synthesis

To 100 mg of γAbu-PS1 peptide in 12 ml of 0.1 M sodium phosphate buffer pH 7.2 was dropwise added 40 mg of SATP-NHS (6 molar equivalents) in 300 µl of DMSO. After 40 minutes, the reaction medium was injected onto C18 RP-MPLC using the same conditions as for γAbu-PS1. SATP-γAbu-PS1 was controlled by MS using negative mode.

| | Yield (%) | Formula | MS expected [M − H]⁻ | MS found [M − H]⁻ |
|---|---|---|---|---|
| SATP-γAbu-PS1 | 76 | $C_{87}H_{104}N_{14}O_{51}S_7$ | 2383.3942 | 2383.3174 |

General Protocol for miniCD4-PS1 Conjugated Molecule Synthesis

SATP-γAbu-PS1 peptide (109 mg) was dissolved in 20 ml of 0.1M sodium phosphate buffer pH 7.2. 50 equivalents (2 ml) of a solution containing 0.5 M Hydroxylamine chlorhydrate in 0.1 M sodium phosphate (pH adjusted to 7.2 by 4N NaOH) were added. After 45 minutes, 52 mg of Lys5/11 (Nε-maleimide) miniCD4 peptide in 22 ml of water were added. After 35 minutes, miniCD4-PS1 conjugate was purified by C18 RP-MPLC using the same conditions as for γAbu-PS1.

Figure 3:
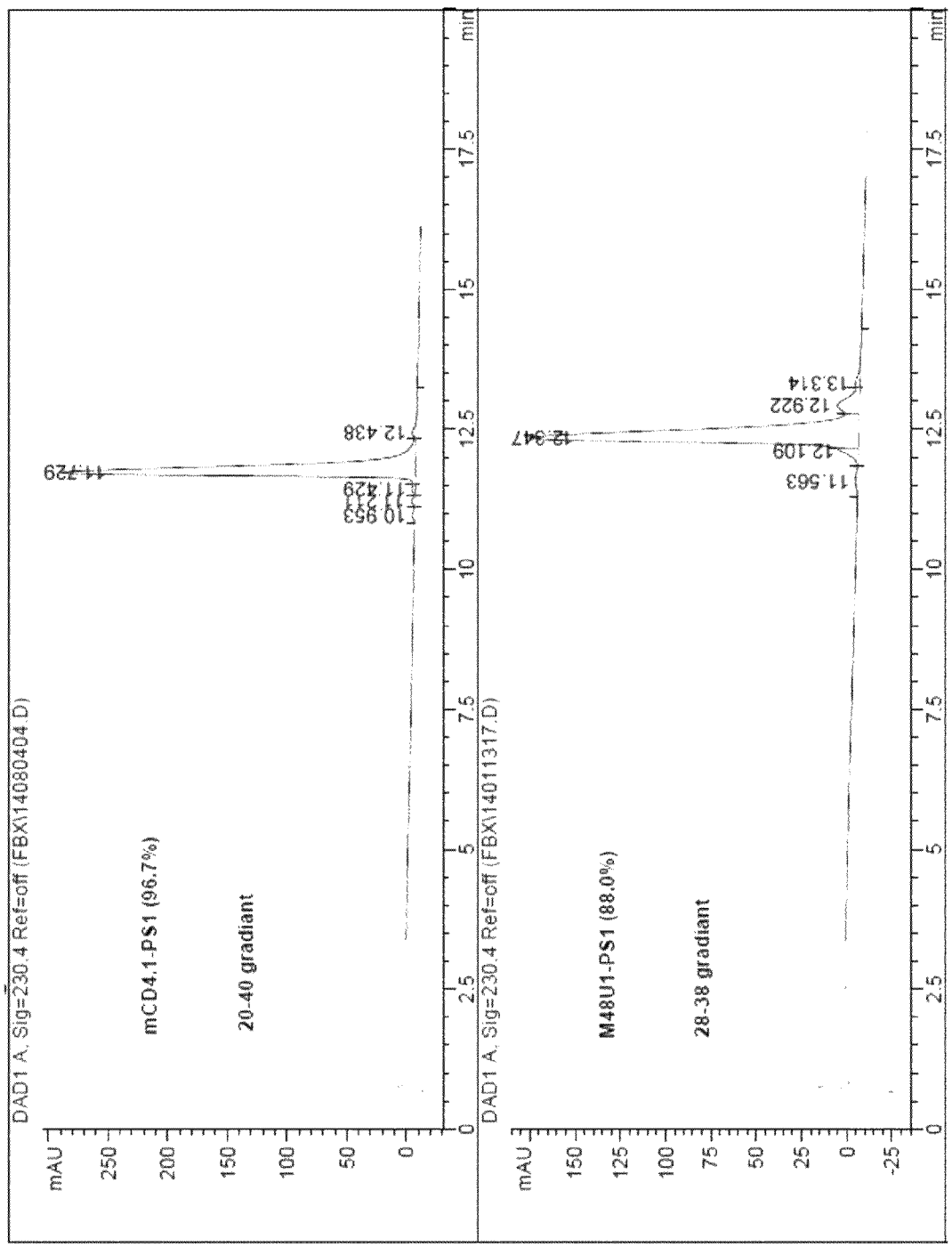
FIG. 3 represents the HPLC profile of reference conjugated molecules (mCD4.1-PS1 and M48U1-PS1).
Figure 4:
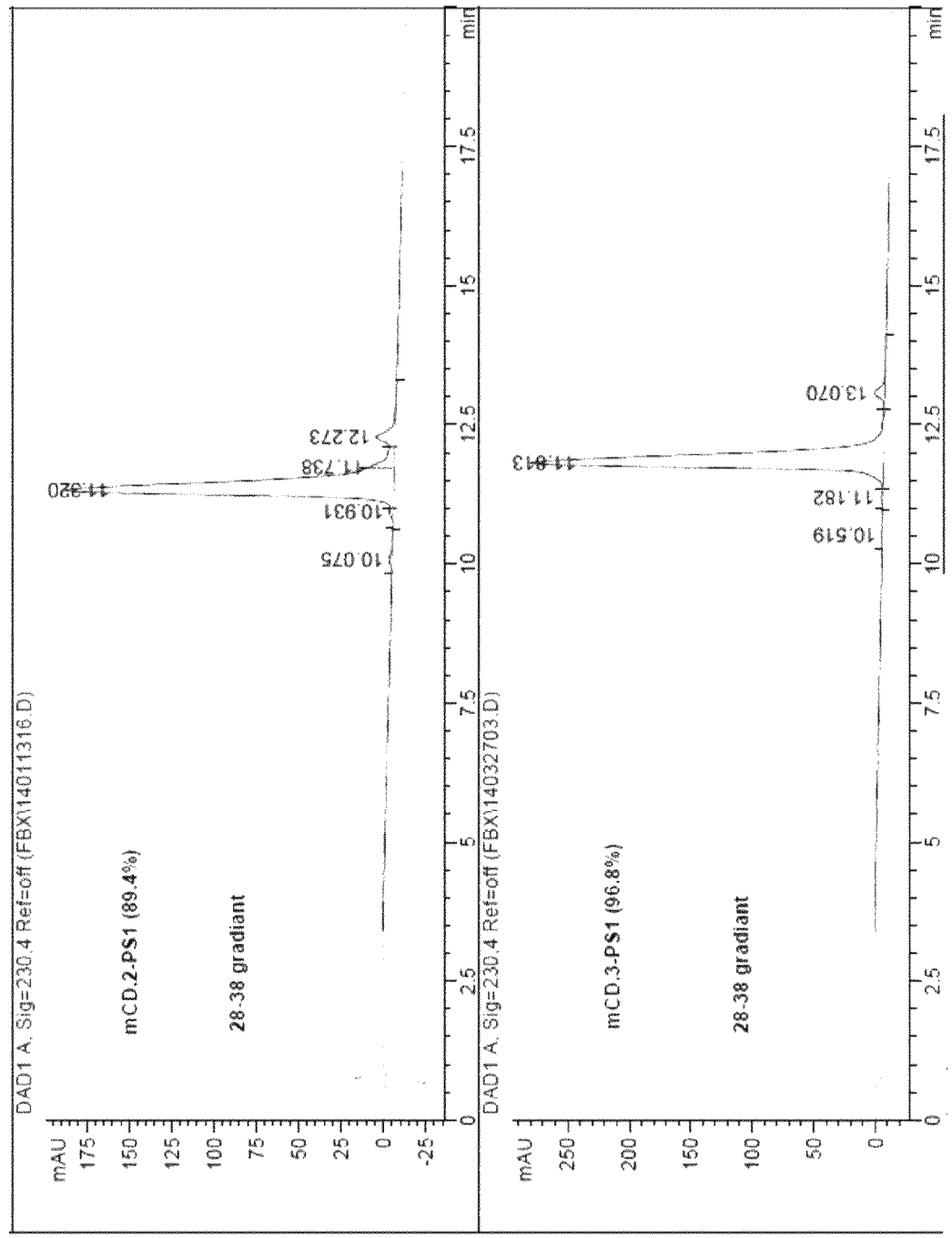
FIG. 4 represents the HPLC profile of conjugated molecules according to the invention (mCD4.2-PS1 and mCD4.3-PS1).
Figure 5:
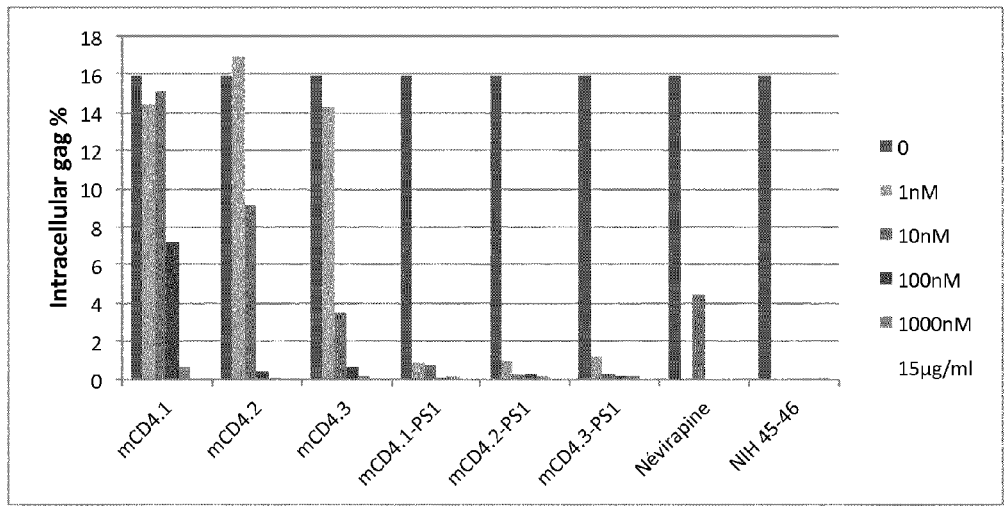
FIG. 5 represent the percentage of intracellular Gag 48 h (FIG. 5A) or 96 h (FIG. 5B) after administration of various compounds at various concentrations in a viral cell-to-cell transmission assay using HIV-1 NL4-3.
Figure 6:
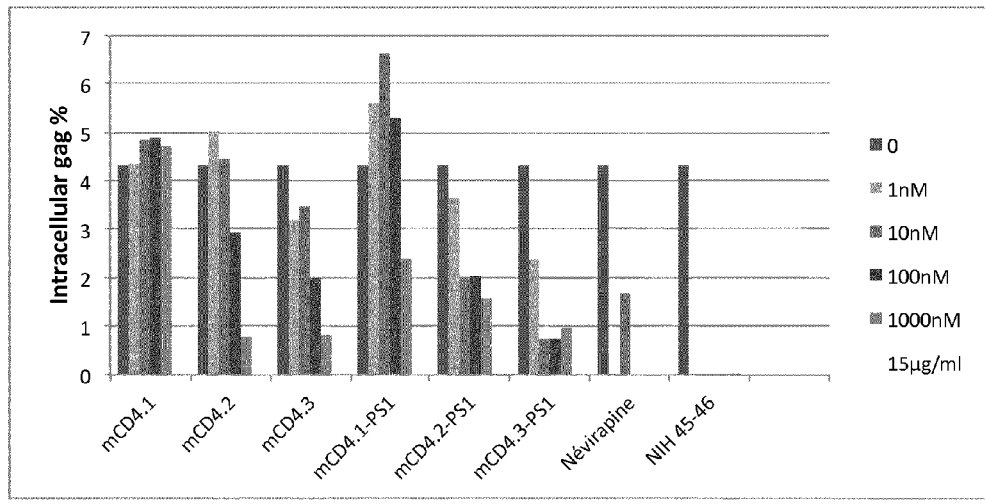
FIG. 6 represent the percentage of intracellular Gag 48 h (FIG. 6A) or 96 h (FIG. 6B) after administration of various compounds at various concentrations in a viral cell-to-cell transmission assay using HIV-1 NLAD8.
Figure 6:
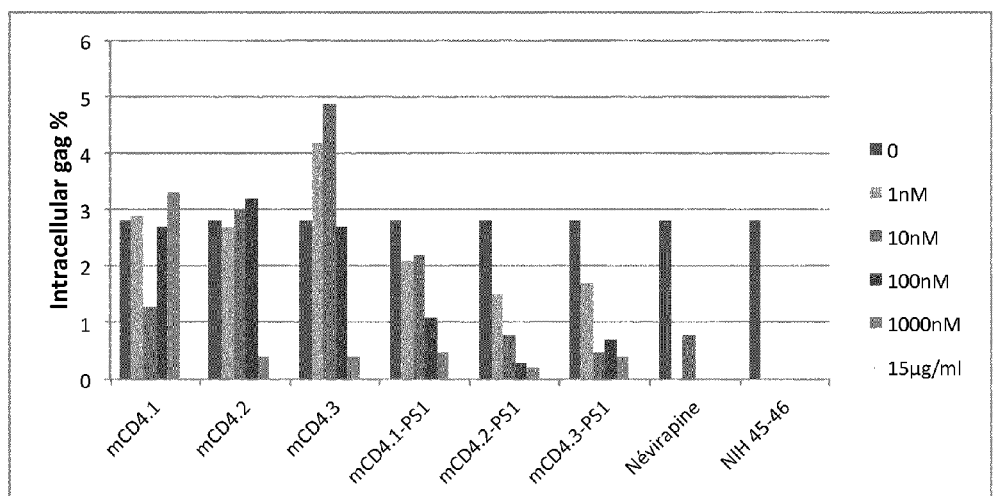
Figure 7:
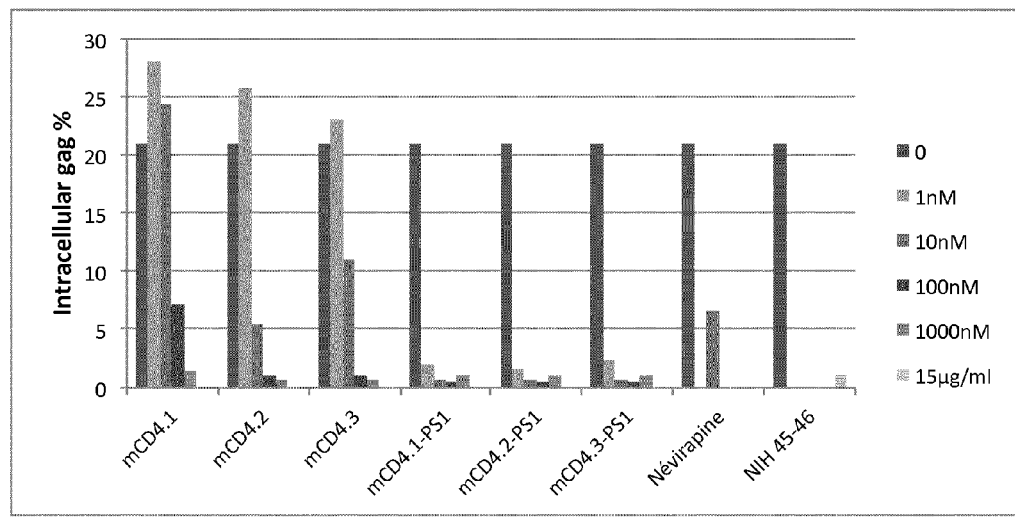
FIG. 7 represent the percentage of intracellular Gag 48 h (FIG. 7A) or 72 h (FIG. 7B) after administration of various compounds at various concentrations in a viral cell-to-cell transmission assay using HIV-1 NL4-3.
Figure 8:
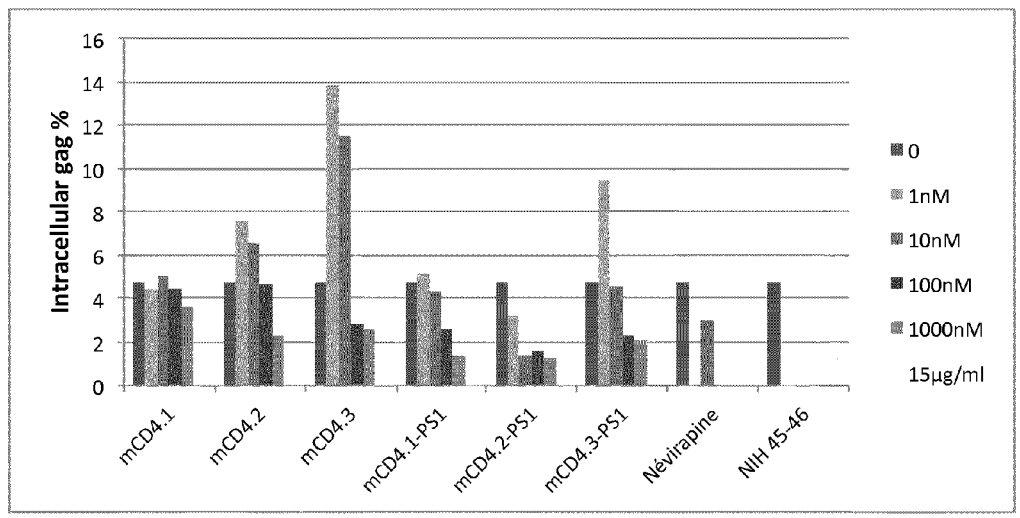
FIG. 8 represent the percentage of intracellular Gag 48 h (FIG. 8A) or 72 h (FIG. 8B) after administration of various compounds at various concentrations in a viral cell-to-cell transmission assay using HIV-1 NLAD8.
Figure 8:
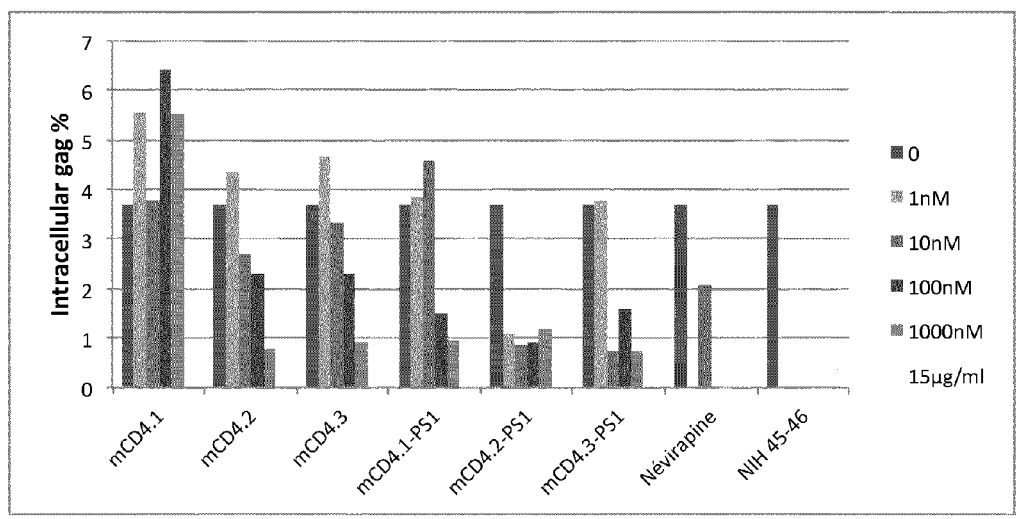

Final purity was controlled by analytical C18 RP-HPLC (AERIS peptide XB-C18, Phenomenex, 3.6 µm, 100×2.1 mm) using a linear gradient of acetonitrile in 100 mM aqueous Trielthylamine acetate buffer over 20 min at 0.35 ml/min flow rate. HPLC profiles are reported on FIGS. 3 and 4. All peptide conjugates were controlled by MS using negative mode.

| Conjugated molecule | Yield (%) | Formula | MS expected [M − H]⁻ | MS found [M − H]⁻ |
|---|---|---|---|---|
| mCD4.1-PS1* | 64 | $C_{221}H_{314}N_{54}O_{88}S_{13}$ | 5552.0933 | 5552.1108 |
| M48U1-PS1* | 61 | $C_{232}H_{332}N_{54}O_{88}S_{13}$ | 5702.3572 | 5702.9180 |
| mCD4.2-PS1 | 66 | $C_{226}H_{328}N_{54}O_{89}S_{13}$ | 5642.2589 | 5642.6030 |
| mCD4.3-PS1 | 66 | $C_{229}H_{335}N_{57}O_{88}S_{13}$ | 5705.9782 | 5705.9243 |

*reference conjugated molecules

Antiviral Activity Assays

The antiviral activity of the tested compounds was determined by pre-incubating 10⁴ TZM-bl cells/well in a 96-well plate for 30 min at 37° C. and 5% $CO_2$ with or without a serial dilution of the compound. Next, 200 $TCID_{50}$ of viruses were added to each well and cultures were incubated for 48 h before luciferase activity was quantified. Each compound was tested in triplicate in a single experiment. Antiviral activity was expressed as the percentage of viral inhibition compared to the untreated control and plotted against the compound concentration. Next, non-linear regression analysis was used to calculate the 50% effective concentration ($EC_{50}$).

Cytotoxic Activity Assays

Cytotoxicity was determined using the water-soluble tetrazolium-1 (WST-1) cell proliferation assay, which is based on the cleavage of the tetrazolium salt WST-1 to a formazan dye by cellular dehydrogenases. Because this bioreduction is dependent on the glycolytic production of NAD(P)H in viable cells, the amount of formazan dye formed is correlated directly to the number of viable cells in a culture. Quantification is performed by measuring absorbance at 450 nm in a multiwell plate reader. An amount of 10⁴ cells was plated per well in a 96-well plate, and a serial dilution of compound was added. Forty eight hours later, cell proliferation reagent was added and cell viability was measured compared to untreated control cultures. Cell viability was plotted against the compound concentration, and nonlinear regression analysis was performed to evaluate the 50% cytotoxic concentration ($CC_{50}$).

Viral Cell-to-Cell Transmission Assays

Primary CD4+ T cells were purified from human peripheral blood by positive selection (Miltenyi). About 98% of cells were CD4+CD3+. For activation, primary T cells were treated with phytohemagglutinin (PHA) (1 µg/ml) for 24 h and then cultured with interleukin 2 (IL-2) (50 IU/ml) for 3-5 days before use. Primary cells were infected with HIV-1 NL4-3 and NLAD8 as described in Lepelley et al. *PLoS Pathog* 2011, 7:e1001284 and Malbec et al. *J Exp Med* 2013, 210:2813-2821. Donor cells were used a few days later, when about 20% of the cells were Gag+. Target cells were labeled with FarRed (2.5 µM; Molecular Probes). Donors were preincubated 1 h with the indicated doses of compounds. Donor and target cells were then mixed at a 1:2 ratio in 96-well plates at a final concentration of $1.5 \times 10^6$/ml in 200 µl, in duplicates. After 48, 72 or 96 h, cells were stained for intracellular Gag (KC57 mAb, Coulter) and analyzed by flow cytometry. When stated, Nevirapine (NVP; 12.5 nM) or the NIH45-46 broadly neutralizing antibody (bNAb) (Malbec et al. *J Exp Med* 2013, 210:2813-2821) was added 1 h before coculture.

Results

Tested Compounds

The following miniCD4 peptides were synthesized as described in the Material and Methods.

| Designation | Sequence | SEQ ID NO |
|---|---|---|
| mCD4.1 | Tpa-NLHK$_5$CQLRCSSLGLLGRCAGS-Bip-CACV-amide | 16 |
| M48U1 | Tpa-NLHFCQLRCK$_{11}$SLGLLGRCApTU$_1$CACV-amide | 17 |
| mCD4.2 | Tpa-NLHK$_5$CQLRCS$_{11}$SLGLLGRCApTU$_1$CACV-amide | 1 |
| mCD4.3 | Tpa-NLHK$_5$CQLRCR$_{11}$SLGLLGRCApTU$_1$CACV-amide | 2 |

The corresponding miniCD4 conjugates, mCD4.1-PS1, M48U1-PS1, mCD4.2-PS1, and mCD4.3-PS1, were synthesized as described in the Material and Methods. mAb VRC01, mAb b12 and Dapivirine (TMC120), used as reference compounds, were obtained from NIH Aids Reagent Program.

Antiviral Activities

The miniCD4 conjugates were then evaluated for their antiviral activity on TZM-bl cells that express Luciferase under the control of the HIV LTR (collaboration G. Vanham, Anvers) according to the protocol described above. All antiviral results are reported in the table below in the form of $EC_{50}$ values (nM).

| Viral strain | Clade-tropism | mCD4.1 | mCD4.1-PS1 | M48U1 | M48U1-PS1 | mCD4.2 | mCD4.2-PS1 | mCD4.3 | mCD4.3-PS1 | mAb VRC01 | mAb b12 | Dapivirine (TMC120) |
|---|---|---|---|---|---|---|---|---|---|---|---|---|
| Bal | B-R5 | 236 | 0.54 | 0.96 | 0.13 | 2 | 0.034 | 2.3 | 0.031 | 0.63 | 1.0 | 1.65 |
| IIIB | B-X4 | 29 | 0.013 | 0.08 | 0.02 | 0.22 | 0.007 | 0.16 | 0.0025 | 0.64 | 0.09 | 0.84 |
| MN | B-X4 | 20 | 0.08 | 0.25 | 0.12 | 0.60 | 0.046 | 0.37 | 0.026 | 2 | 1.5 | 1.5 |
| SHIV162p3 | B-R5 | 5372 | 36 | 24 | 3.4 | 69 | 2.2 | 29 | 1.4 | 8.2 | 5.9 | >1000 |
| SF162 | B-R5 | 130 | 0.11 | 1 | 0.05 | 1.24 | 0.01 | 0.66 | 0.008 | 6.0 | 0.43 | 1.3 |
| VI829 | C-R5 | >10000 | 16 | 59 | 1.1 | 512 | 4.0 | 221 | 3.6 | 9.2 | >100 | 1.3 |
| VI820 | A-X4R5 | 1686 | 25 | 3.8 | 0.1 | 6.1 | 0.031 | 4.2 | 0.024 | 11.9 | >100 | 1.95 |
| VI1888 (CRF01) | AE-R5 | >1000 | 1102 | 8422 | 1069 | 9763 | 1064 | 8018 | 1212 | 16 | 60 | 2.1 |
| MP568 (CRF02) | AG-R5 | 7931 | 310 | 129 | 15 | 155 | 4.9 | 204 | 4.2 | 54 | >100 | 1.1 |
| VI824 | D-R5 | 3176 | 40 | 29 | 2.2 | 56 | 0.68 | 39 | 0.7 | >100 | >100 | 1.2 |
| Ca10-3 (CRF01) | AE-X4 | 96 | 0.57 | 2.7 | 0.6 | 4.73 | 0.12 | 3.1 | 0.076 | 13 | >100 | 1.3 |
| p246F10 | C-R5 | >10000 | 723 |  |  | 718 | 58 | 510 | 33 | 85 | >100 | 1.4 |
| pREJO.c/286 4 cl2 | B-R5 | 108 | 0.66 |  |  | 76 | 0.27 | 46 | 0.28 | 0.77 | >100 | 1.6 |

Cytotoxic Activities

The miniCD4 conjugates were then evaluated for their cytotoxic activity according to the protocol described above. All cytotoxic results are reported in the table below in the form of $CC_{50}$ values (nM).

|  | mCD4.1 | mCD4.1-PS1 | M48U1 | M48U1-PS1 | mCD4.2 | mCD4.2-PS1 | mCD4.3 | mCD4.3-PS1 |
|---|---|---|---|---|---|---|---|---|
| CC50 | 45525 | >50000 | 12946 | >50000 | 24036 | >50000 | 15540 | >50000 |

|  | mAb VRC01 | mAb b12 | Dapivirine (TMC 120) |
|---|---|---|---|
| CC50 | >100 | >300 | 2524 |

Viral Cell-to-Cell Transmission Inhibition mCD4.1, mCD4.2, mCD4.3 and their PS1 conjugates, as well as Nevirapine and NIH45-46, were evaluated for their capacity to inhibit cell-cell HIV transmission. This was performed using primary cells infected with R5 (HIV1-NLAD8) and X4 (HIV1-NL4-3) viruses.

The results obtained are presented on FIGS. 5A, 5B, 6A, 6B, 7A, 7B, 8A and 8B.

DISCUSSION

Results from antiviral activities clearly show the great enhancement of miniCD4 peptides activity brought by polyanion (PS1) coupling. The effect of polyanion coupling is still important on miniCD4 peptides that are already very active like M48U1, mCD4.2 and mCD4.3. These results confirm the synergetic effect afforded by polyanion covalent coupling. In particular, the polyanion coupling greatly enhances antiviral activity of MCD4.2-PS1 as compared to mCD4.2 alone (9-190 fold increase).

The two conjugates according to the invention (mCD4.2-PS1 and mCD4.3-PS1) also show enhanced activity on Circulating Recombinant Form (5CRF) strains that are difficult to inhibit. $EC_{50}$ of 4.9 nM and 1.1 μm respectively for CRF02_AG R5 and CRF01_AE R5 were obtained for mCD4.2-PS1.

It is worth noting that these molecules display much higher antiHIV activity than VRC01, currently considered as one of the most potent broadly neutralising antibody.

Importantly, these conjugates display an extraordinary selective index (SI) of 1 to 5.106 when measured on TZM-bl cells (SI=CC50/$EC_{50}$). Moreover, polyanion coupling seems to decrease at least by two fold the toxicity of the uncoupled miniCD4.

The conjugate according to the invention mCD4.2-PS1 displays $EC_{50}$ as low as 34 pM (Bal strain, B-R5) and 10 pM (SF162 strain, B-R5).

When compared to mCD4.1-PS1, a 25 fold increase of HIV antiviral activity has been obtained with mCD4.2-PS1 for R5 strains Ba_L (0.034 nM versus 0.54 nM) and SF162.

It is worth noting that polyanion coupling in position 5 of miniCD4 peptides rather than in position 11 leads to more active compounds. When compared to M48U1-PS1 (polyanion coupled on Lys11), mCD4.2-PS1 and mCD4.3-PS1 (polyanion coupled on Lys5) show a 1.5 to 5 fold increase in antiviral activity.

Moreover, on the way to develop a new anti-HIV drug, cell-cell transmission inhibition has also to be evaluated since this form of dissemination appears to be less susceptible to inhibition by antiretroviral drugs than cell-free virus transmission. Even though cell-cell transmission is more difficult to inhibit for R5 viruses than for X4 viruses, mCD4.2-PS1 and mCD4.3-PS1 were able to block cell-cell virus transmission for both viruses (mCD4.1-PS1 also but to a lesser extend). These results are very encouraging when comparing the low molecular conjugates according to the invention (around 5.5 Kd) to the broadly neutralizing antibody NIH45-46 (150 Kd), targeting the CD4 binding site of gp120, used as reference at a 15 μg/ml (100 nM). These experiments also confirmed the great importance of PS1 conjugation in enhancing miniCD4 peptides antiviral activity.

The invention claimed is:

1. A conjugated molecule comprising a peptide derived from the CD4 receptor, said peptide being coupled to an organic molecule by means of a linker, wherein:

the said peptide derived from the CD4 receptor comprises the following general sequence (I):

Xaa$^f$-P1-Lys-Cys-P2-Cys-P3-Cys-Xaa$^g$-Xaa$^h$-Xaa$^i$-Xaa$^j$-Cys-Xaa$^k$-Cys-Xaa$^l$-Xaa$^m$, (I)

in which:
P1 represents 3 to 6 amino acid residues,
P2 represents 2 to 4 amino acid residues,
P3 represents 6 to 10 amino acid residues,
Xaa$^f$ represents N-acetylcysteine (Ac-Cys) or thiopropionic acid (TPA),
Xaa$^g$ represents Ala,
Xaa$^h$ represents D-proline,
Xaa$^i$ represents Thr,
Xaa$^j$ represents biphenylalanine (Bip), phenylalanine, [beta]-naphthylalanine or 4-cyclohexylmethoxy-L-phenylalanine (U$_1$),
Xaa$^k$ represents Thr or Ala,
Xaa$^l$ represents Gly, Val or Leu, and
Xaa$^m$ represents —NH$_2$ or —OH, the amino acid residues in P1, P2 and P3 being natural or non-natural, identical or different, said residues of P1, P2 and P3 being all different from the Lys residue and P1, P2 and P3 having a sequence in common or not, and the said organic molecule comprises
an anionic polypeptide consisting of 5 to 21 amino acid residues being natural or non-natural, identical or different, wherein at least 3 amino acids are negatively charged, and
a molecular group A-Z, wherein:
A comprises a group chosen between the groups of formula —CO(CH$_2$)$_p$—NH—CO—(CH$_2$)$_q$—, —CO(CH$_2$—CH$_2$)—(O—CH$_2$—CH$_2$)$_p$—NH—CO—(CH$_2$)$_q$—, —CO(CH$_2$)$_p$—NH—CO—(CH$_2$—CH$_2$—O)$_q$—(CH$_2$—CH$_2$)— and —CO(CH$_2$—CH$_2$)—(O—CH$_2$—CH$_2$)$_p$—NH—CO—(CH$_2$—CH$_2$—O)$_q$—(CH$_2$—CH$_2$)—, wherein p represents an integer comprised between 1 and 10 and q represents an integer comprised between 1 and 10, and Z represents a halogen atom, a thiol or a maleimide group,
wherein the first carbonyl group of A is coupled to the N-terminal end of the anionic polypeptide,
wherein the said linker is covalently bound at one of its extremity to the free amino group (—NH$_2$) of the amino acid residue Lys present in general sequence (I) of the said peptide derived from the CD4 receptor, and is covalently bound at its other extremity to the Z group of the said organic molecule when Z is a thiol or a maleimide group or to the A group of the said organic molecule when Z is a halogen atom, Z being eliminated in this last case.

2. The conjugated molecule according to claim 1, wherein P1 represents 3 amino acid residues.

3. The conjugated molecule according to claim 1, wherein the anionic polypeptide consists of 10 to 17 amino acid residues being natural or non-natural, identical or different, wherein 3 to 15 amino acids are negatively charged.

4. The conjugated molecule according to claim 1, wherein Xaa$^j$ represents 4-cyclohexylmethoxy-L-phenylalanine (U$_1$).

5. The conjugated molecule according to claim 1, wherein the sequence of the peptide derived from the CD4 receptor of general sequence (I) is chosen from the group consisting of sequences SEQ ID NO: 1, SEQ ID NO: 2, SEQ ID NO: 20 and SEQ ID NO: 21.

6. The conjugated molecule according to claim 1, wherein the linker is chosen from the group consisting of:

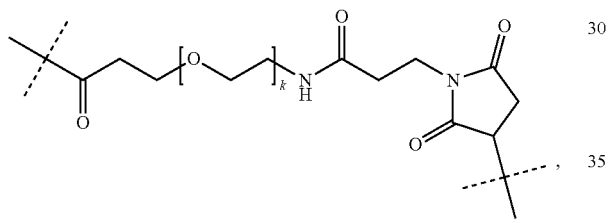

with k representing an integer comprised between 2 and 24,

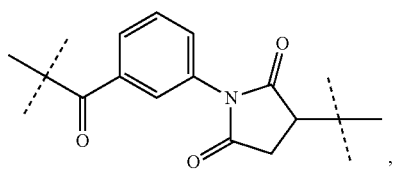

with k1 representing an integer equal to 1, 2, 3, 5 and 10,

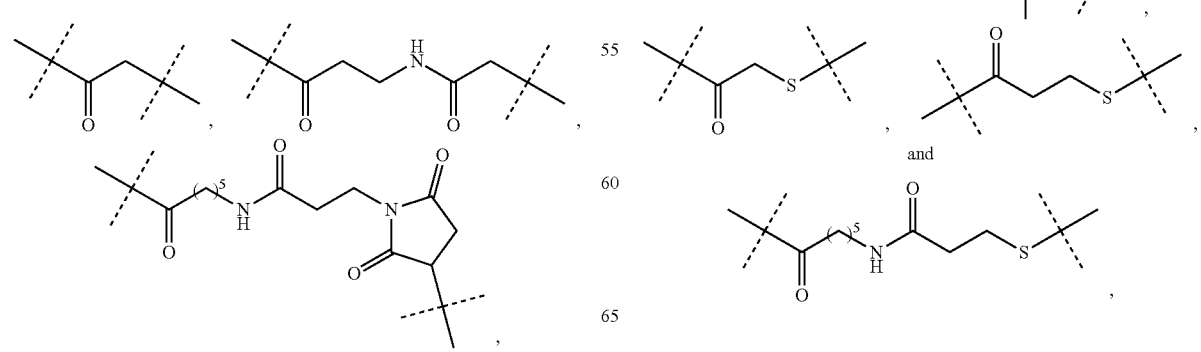

when Z represents a thiol group, and among:

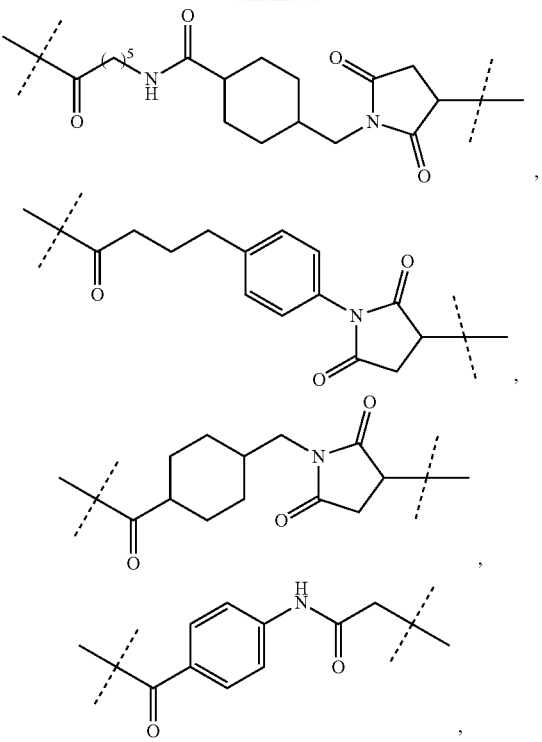

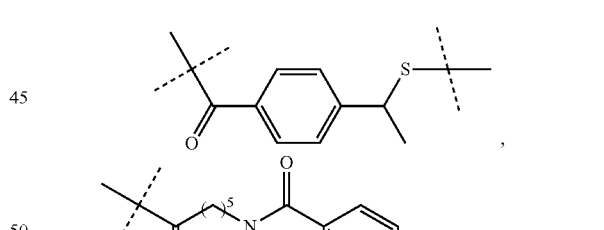

when Z represents a maleimide group or a halogen atom.

7. The conjugated molecule according to claim 1, wherein the negatively charged amino acids of the anionic polypeptide are chosen among aspartic acid, sulfotyrosine, tyrosine sulfonate, aminosuberic acid, p-carboxymethyl phenylalanine, and glutamic acid, wherein said sulfotyrosine has the formula:

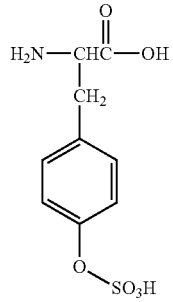

wherein said tyrosine sulfonate has the formula:

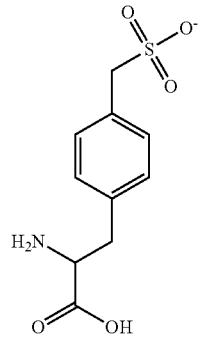 [SMILES: NC(Cc1ccc(CS(=O)(=O)[O-])cc1)C(=O)O]

wherein said aminosuberic acid has the formula:

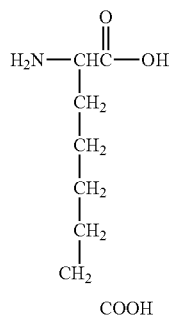

and wherein said p-carboxymethyl phenylalanine has the formula:

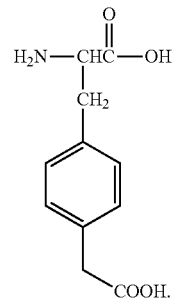

8. The conjugated molecule according to claim 1, wherein the anionic polypeptide consists of 13 amino acids.

9. The conjugated molecule according to claim 1, wherein the anionic polypeptide comprises at least two different amino acids.

10. The conjugated molecule according to claim 9, wherein the anionic polypeptide comprises at least aspartic acid (D) and serine (S).

11. The conjugated molecule according to claim 9, wherein said anionic polypeptide has a sequence of S-(X-D-X-S)$_n$, where n represents an integer comprised between 1 and 5, S represents serine, D represents aspartic acid, X is selected from the group consisting of: tyrosine, sulfotyrosine, tyrosine sulfonate, aminosuberic acid, and p-carboxymethyl phenylalanine and where the various X groups are identical or different.

12. The conjugated molecule according to claim 11, wherein said anionic polypeptide has a sequence of S-X-D-X-S-X-D-X-S-X-D-X-S (SEQ ID NO: 19), wherein S represents serine, D represents aspartic acid, X is selected from the group consisting of: tyrosine, sulfotyrosine, tyrosine sulfonate, aminosuberic acid, and p-carboxymethyl phenylalanine and where the various X groups are identical or different.

13. The conjugated molecule according to claim 11, wherein X groups are identical.

14. The conjugated molecule according to claim 11, wherein said anionic polypeptide has a sequence which is selected in the group consisting of: S-(Y-D-Y-S)$_n$, S-(Y$_{SO3}$-D-Y$_{SO3}$-S)$_n$, S-(Y$_{SN}$-D-Y$_{SN}$-S)$_n$, S-(pF-D-pF-S)$_n$, and S-(Asu-D-Asu-S)$_n$, where n represents an integer comprised between 1 and 5, S represents serine, D represents aspartic acid, Y represents tyrosine, Y$_{SO3}$ represents sulfotyrosine, Y$_{SN}$ represents tyrosine sulfonate, pF represents p-carboxymethyl phenylalanine and Asu represents aminosuberic acid.

15. The conjugated molecule according to claim 11, wherein said anionic polypeptide has a sequence which is selected in the group consisting of: S-Y-D-Y-S-Y-D-Y-S-Y-D-Y-S (SEQ ID NO: 8), S-Y$_{SO3}$-D-Y$_{SO3}$-S-Y$_{SO3}$-D-Y$_{SO3}$-S-Y$_{SO3}$-D-Y$_{SO3}$-S (SEQ ID NO: 4), S-Y$_{SN}$-D-Y$_{SN}$-S-Y$_{SN}$-D-Y$_{SN}$-S-Y$_{SN}$-D-Y$_{SN}$-S(SEQ ID NO: 5), S-pF-D-pF-S-pF-D-pF-S-pF-D-pF-S(SEQ ID NO: 6), S-Asu-D-Asu-S-Asu-D-Asu-S-Asu-D-Asu-S (SEQ ID NO: 7), S-Y$_{SO3}$-D-Y$_{SO3}$-S-Y$_{SO3}$-D-Y-S-Y-D-Y-S(SEQ ID NO: 14), and S-Y-D-Y-S-Y-D-Y$_{SO3}$-S-Y$_{SO3}$-D-Y$_{SO3}$-S(SEQ ID NO: 15), where S represents serine, D represents aspartic acid, Y represents tyrosine, Y$_{SO3}$ represents sulfotyrosine, Y$_{SN}$ represents tyrosine sulfonate, pF represents p-carboxymethyl phenylalanine and Asu represents aminosuberic acid.

16. The conjugated molecule according to claim 1, wherein:

the peptide derived from the CD4 receptor is chosen from the group consisting of sequences SEQ ID NO: 1, SEQ ID NO: 2, SEQ ID NO: 20 and SEQ ID NO: 21, the linker is CO—$(CH_2CH_2O)_2CH_2CH_2NHCO(CH_2)_2$-pyrrolidinyl-2,5-dione, the organic molecule comprises an anionic polypeptide having the following sequence S-$Y_{SO3}$-D-$Y_{SO3}$-S-$Y_{SO3}$-D-$Y_{SO3}$-S-$Y_{SO3}$-D-$Y_{SO3}$-S as defined in claim 15, which is linked to the linker by a molecular group of formula A-Z, wherein A is —$CO(CH_2)_3NH$—CO$(CH_2)_2$— and Z is a thiol group.

17. A method for treating AIDS comprising the administration to a person in need thereof of an effective amount of a conjugated molecule according to a claim 1.

18. A method for inhibiting the HIV cell-to-cell transmission comprising the administration to a person in need thereof of an effective amount of a conjugated molecule according to claim 1.

19. A pharmaceutical composition comprising a conjugated molecule according to claim 1 and a pharmaceutically acceptable vehicle.

20. A process for the preparation of a conjugated molecule according to claim 1 comprising the following steps:

a. contacting the miniCD4 peptide of general sequence (I) as defined in claim 1 with a bifunctional compound carrying two active groups, so that one of the two active groups forms a covalent bond with the free amino group (—$NH_2$) of the residue of the amino acid Lys present in general sequence (I), in order to obtain an activated peptide carrying the second active group of the bifunctional group, and b. contacting the activated peptide obtained at step (a) with an organic molecule as defined in claim 1, wherein Z can be in a protected form when Z is a thiol group, so that the active group of the activated peptide reacts with the Z group of the organic molecule to form a covalent bond between the organic molecule and the activated peptide, in order to obtain the conjugated molecule.

* * * * *

SEQUENCE LISTING

```
<160> NUMBER OF SEQ ID NOS: 21

<210> SEQ ID NO 1
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: MOD_RES
<222> LOCATION: (20)..(20)
<223> OTHER INFORMATION: D-proline
<220> FEATURE:
<221> NAME/KEY: MISC_FEATURE
<222> LOCATION: (22)..(22)
<223> OTHER INFORMATION: Phe is a 4-cyclohexylmethoxy-L-phenylalanine
<220> FEATURE:
<221> NAME/KEY: MOD_RES
<222> LOCATION: (26)..(26)
<223> OTHER INFORMATION: AMIDATION

<400> SEQUENCE: 1

Asn Leu His Lys Cys Gln Leu Arg Cys Ser Ser Leu Gly Leu Leu Gly
1               5                   10                  15

Arg Cys Ala Pro Thr Phe Cys Ala Cys Val
            20                  25

<210> SEQ ID NO 2
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: MOD_RES
<222> LOCATION: (20)..(20)
<223> OTHER INFORMATION: D-proline
<220> FEATURE:
<221> NAME/KEY: MISC_FEATURE
<222> LOCATION: (22)..(22)
```

<223> OTHER INFORMATION: Phe is a 4-cyclohexylmethoxy-L-phenylalanine
<220> FEATURE:
<221> NAME/KEY: MOD_RES
<222> LOCATION: (26)..(26)
<223> OTHER INFORMATION: AMIDATION

<400> SEQUENCE: 2

Asn Leu His Lys Cys Gln Leu Arg Cys Arg Ser Leu Gly Leu Leu Gly
1               5                   10                  15

Arg Cys Ala Pro Thr Phe Cys Ala Cys Val
            20                  25

<210> SEQ ID NO 3
<211> LENGTH: 13
<212> TYPE: PRT
<213> ORGANISM: artificial
<220> FEATURE:
<223> OTHER INFORMATION: Anionic polypeptide consisting of 13 glutamic
      acid residues

<400> SEQUENCE: 3

Glu Glu Glu Glu Glu Glu Glu Glu Glu Glu Glu Glu Glu
1               5                   10

<210> SEQ ID NO 4
<211> LENGTH: 13
<212> TYPE: PRT
<213> ORGANISM: artificial
<220> FEATURE:
<223> OTHER INFORMATION: Anionic polypeptide
<220> FEATURE:
<221> NAME/KEY: MOD_RES
<222> LOCATION: (2)..(2)
<223> OTHER INFORMATION: SULFATATION (sulfo tyrosine)
<220> FEATURE:
<221> NAME/KEY: MOD_RES
<222> LOCATION: (4)..(4)
<223> OTHER INFORMATION: SULFATATION (sulfo tyrosine)
<220> FEATURE:
<221> NAME/KEY: MOD_RES
<222> LOCATION: (6)..(6)
<223> OTHER INFORMATION: SULFATATION (sulfo tyrosine)
<220> FEATURE:
<221> NAME/KEY: MOD_RES
<222> LOCATION: (8)..(8)
<223> OTHER INFORMATION: SULFATATION (sulfo tyrosine)
<220> FEATURE:
<221> NAME/KEY: MOD_RES
<222> LOCATION: (10)..(10)
<223> OTHER INFORMATION: SULFATATION (sulfo tyrosine)
<220> FEATURE:
<221> NAME/KEY: MOD_RES
<222> LOCATION: (12)..(12)
<223> OTHER INFORMATION: SULFATATION (sulfo tyrosine)

<400> SEQUENCE: 4

Ser Tyr Asp Tyr Ser Tyr Asp Tyr Ser Tyr Asp Tyr Ser
1               5                   10

<210> SEQ ID NO 5
<211> LENGTH: 13
<212> TYPE: PRT
<213> ORGANISM: artificial
<220> FEATURE:
<223> OTHER INFORMATION: Anionic polypeptide
<220> FEATURE:
<221> NAME/KEY: MOD_RES
<222> LOCATION: (2)..(2)
<223> OTHER INFORMATION: Tyr is a tyrosine sulfonate
<220> FEATURE:
<221> NAME/KEY: MOD_RES
<222> LOCATION: (4)..(4)

```
<223> OTHER INFORMATION: Tyr is a tyrosine sulfonate
<220> FEATURE:
<221> NAME/KEY: MOD_RES
<222> LOCATION: (6)..(6)
<223> OTHER INFORMATION: Tyr is a tyrosine sulfonate
<220> FEATURE:
<221> NAME/KEY: MOD_RES
<222> LOCATION: (8)..(8)
<223> OTHER INFORMATION: Tyr is a tyrosine sulfonate
<220> FEATURE:
<221> NAME/KEY: MOD_RES
<222> LOCATION: (10)..(10)
<223> OTHER INFORMATION: Tyr is a tyrosine sulfonate
<220> FEATURE:
<221> NAME/KEY: MOD_RES
<222> LOCATION: (12)..(12)
<223> OTHER INFORMATION: Tyr is a tyrosine sulfonate

<400> SEQUENCE: 5

Ser Tyr Asp Tyr Ser Tyr Asp Tyr Ser Tyr Asp Tyr Ser
1               5                   10

<210> SEQ ID NO 6
<211> LENGTH: 13
<212> TYPE: PRT
<213> ORGANISM: artificial
<220> FEATURE:
<223> OTHER INFORMATION: anionic polypeptide
<220> FEATURE:
<221> NAME/KEY: misc_feature
<222> LOCATION: (2)..(2)
<223> OTHER INFORMATION: Phe is a p-Carboxymethyl Phe
<220> FEATURE:
<221> NAME/KEY: misc_feature
<222> LOCATION: (4)..(4)
<223> OTHER INFORMATION: Phe is a p-Carboxymethyl Phe
<220> FEATURE:
<221> NAME/KEY: misc_feature
<222> LOCATION: (6)..(6)
<223> OTHER INFORMATION: Phe is a p-Carboxymethyl Phe
<220> FEATURE:
<221> NAME/KEY: misc_feature
<222> LOCATION: (8)..(8)
<223> OTHER INFORMATION: Phe is a p-Carboxymethyl Phe
<220> FEATURE:
<221> NAME/KEY: misc_feature
<222> LOCATION: (10)..(10)
<223> OTHER INFORMATION: Phe is a p-Carboxymethyl Phe
<220> FEATURE:
<221> NAME/KEY: misc_feature
<222> LOCATION: (12)..(12)
<223> OTHER INFORMATION: Phe is a p-Carboxymethyl Phe

<400> SEQUENCE: 6

Ser Phe Asp Phe Ser Phe Asp Phe Ser Phe Asp Phe Ser
1               5                   10

<210> SEQ ID NO 7
<211> LENGTH: 13
<212> TYPE: PRT
<213> ORGANISM: artificial
<220> FEATURE:
<223> OTHER INFORMATION: anionic polypeptide
<220> FEATURE:
<221> NAME/KEY: misc_feature
<222> LOCATION: (2)..(2)
<223> OTHER INFORMATION: Xaa represents a Aminosuberic acid
<220> FEATURE:
<221> NAME/KEY: misc_feature
<222> LOCATION: (4)..(4)
<223> OTHER INFORMATION: Xaa represents a Aminosuberic acid
<220> FEATURE:
<221> NAME/KEY: misc_feature
<222> LOCATION: (6)..(6)
<223> OTHER INFORMATION: Xaa represents a Aminosuberic acid
```

```
<220> FEATURE:
<221> NAME/KEY: misc_feature
<222> LOCATION: (8)..(8)
<223> OTHER INFORMATION: Xaa represents a Aminosuberic acid
<220> FEATURE:
<221> NAME/KEY: misc_feature
<222> LOCATION: (10)..(10)
<223> OTHER INFORMATION: Xaa represents a Aminosuberic acid
<220> FEATURE:
<221> NAME/KEY: misc_feature
<222> LOCATION: (12)..(12)
<223> OTHER INFORMATION: Xaa represents a Aminosuberic acid

<400> SEQUENCE: 7

Ser Xaa Asp Xaa Ser Xaa Asp Xaa Ser Xaa Asp Xaa Ser
1               5                   10

<210> SEQ ID NO 8
<211> LENGTH: 13
<212> TYPE: PRT
<213> ORGANISM: artificial
<220> FEATURE:
<223> OTHER INFORMATION: anionic polypeptide

<400> SEQUENCE: 8

Ser Tyr Asp Tyr Ser Tyr Asp Tyr Ser Tyr Asp Tyr Ser
1               5                   10

<210> SEQ ID NO 9
<211> LENGTH: 13
<212> TYPE: PRT
<213> ORGANISM: artificial
<220> FEATURE:
<223> OTHER INFORMATION: anionic polypeptide consisting of 13 aspartic
      acid residues

<400> SEQUENCE: 9

Asp Asp Asp Asp Asp Asp Asp Asp Asp Asp Asp Asp Asp
1               5                   10

<210> SEQ ID NO 10
<211> LENGTH: 13
<212> TYPE: PRT
<213> ORGANISM: artificial
<220> FEATURE:
<223> OTHER INFORMATION: anionic polypeptide consisting of 13
      sulfotyrosine residues
<220> FEATURE:
<221> NAME/KEY: MOD_RES
<222> LOCATION: (1)..(13)
<223> OTHER INFORMATION: SULFATATION (sulfo tyrosine)

<400> SEQUENCE: 10

Tyr Tyr Tyr Tyr Tyr Tyr Tyr Tyr Tyr Tyr Tyr Tyr Tyr
1               5                   10

<210> SEQ ID NO 11
<211> LENGTH: 13
<212> TYPE: PRT
<213> ORGANISM: artificial
<220> FEATURE:
<223> OTHER INFORMATION: anionic polypeptide consisting of 13 tyrosine
      sulfonate residues
<220> FEATURE:
<221> NAME/KEY: MOD_RES
<222> LOCATION: (1)..(13)
<223> OTHER INFORMATION: Tyr is a tyrosine sulfonate

<400> SEQUENCE: 11

Tyr Tyr Tyr Tyr Tyr Tyr Tyr Tyr Tyr Tyr Tyr Tyr Tyr
```

-continued

```
1               5                   10

<210> SEQ ID NO 12
<211> LENGTH: 13
<212> TYPE: PRT
<213> ORGANISM: artificial
<220> FEATURE:
<223> OTHER INFORMATION: anionic polypeptide consisting of 13
      aminosuberic acid
<220> FEATURE:
<221> NAME/KEY: misc_feature
<222> LOCATION: (1)..(13)
<223> OTHER INFORMATION: Xaa represents a Aminosuberic acid

<400> SEQUENCE: 12

Xaa Xaa Xaa Xaa Xaa Xaa Xaa Xaa Xaa Xaa Xaa Xaa Xaa
1               5                   10

<210> SEQ ID NO 13
<211> LENGTH: 13
<212> TYPE: PRT
<213> ORGANISM: artificial
<220> FEATURE:
<223> OTHER INFORMATION: anionic peptide consisting of 13
      p-Carboxymethyl phenylalanine
<220> FEATURE:
<221> NAME/KEY: misc_feature
<222> LOCATION: (1)..(13)
<223> OTHER INFORMATION: Phe is a p-Carboxymethyl Phe

<400> SEQUENCE: 13

Phe Phe Phe Phe Phe Phe Phe Phe Phe Phe Phe Phe Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Anionic polypeptide
<220> FEATURE:
<221> NAME/KEY: MOD_RES
<222> LOCATION: (2)..(2)
<223> OTHER INFORMATION: SULFATATION (sulfo tyrosine)
<220> FEATURE:
<221> NAME/KEY: MOD_RES
<222> LOCATION: (4)..(4)
<223> OTHER INFORMATION: SULFATATION (sulfo tyrosine)
<220> FEATURE:
<221> NAME/KEY: MOD_RES
<222> LOCATION: (6)..(6)
<223> OTHER INFORMATION: SULFATATION (sulfo tyrosine)

<400> SEQUENCE: 14

Ser Tyr Asp Tyr Ser Tyr Asp Tyr Ser Tyr Asp Tyr Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Anionic polypeptide
<220> FEATURE:
<221> NAME/KEY: MOD_RES
<222> LOCATION: (8)..(8)
<223> OTHER INFORMATION: SULFATATION (sulfo tyrosine)
<220> FEATURE:
<221> NAME/KEY: MOD_RES
<222> LOCATION: (10)..(10)
<223> OTHER INFORMATION: SULFATATION (sulfo tyrosine)
<220> FEATURE:
```

```
<221> NAME/KEY: MOD_RES
<222> LOCATION: (12)..(12)
<223> OTHER INFORMATION: SULFATATION (sulfo tyrosine)

<400> SEQUENCE: 15

Ser Tyr Asp Tyr Ser Tyr Asp Tyr Ser Tyr Asp Tyr Ser
1               5                   10

<210> SEQ ID NO 16
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: misc_feature
<222> LOCATION: (22)..(22)
<223> OTHER INFORMATION: Phe is a Bi-phenylalanine
<220> FEATURE:
<221> NAME/KEY: MOD_RES
<222> LOCATION: (26)..(26)
<223> OTHER INFORMATION: AMIDATION

<400> SEQUENCE: 16

Asn Leu His Lys Cys Gln Leu Arg Cys Ser Ser Leu Gly Leu Leu Gly
1               5                   10                  15

Arg Cys Ala Gly Ser Phe Cys Ala Cys Val
            20                  25

<210> SEQ ID NO 17
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: MOD_RES
<222> LOCATION: (20)..(20)
<223> OTHER INFORMATION: D-Proline
<220> FEATURE:
<221> NAME/KEY: MISC_FEATURE
<222> LOCATION: (22)..(22)
<223> OTHER INFORMATION: Phe is a 4-cyclohexylmethoxy-L-phenylalanine
<220> FEATURE:
<221> NAME/KEY: MOD_RES
<222> LOCATION: (26)..(26)
<223> OTHER INFORMATION: AMIDATION

<400> SEQUENCE: 17

Asn Leu His Phe Cys Gln Leu Arg Cys Lys Ser Leu Gly Leu Leu Gly
1               5                   10                  15

Arg Cys Ala Pro Thr Phe Cys Ala Cys Val
            20                  25

<210> SEQ ID NO 18
<211> LENGTH: 13
<212> TYPE: PRT
<213> ORGANISM: artificial
<220> FEATURE:
<223> OTHER INFORMATION: Polyanionic peptide gAbu-PS1
<220> FEATURE:
<221> NAME/KEY: BINDING
<222> LOCATION: (1)..(1)
```

<223> OTHER INFORMATION: NH2-(CH2)3-CO-Ser
<220> FEATURE:
<221> NAME/KEY: MOD_RES
<222> LOCATION: (2)..(2)
<223> OTHER INFORMATION: SULFATATION (sulfo tyrosine)
<220> FEATURE:
<221> NAME/KEY: MOD_RES
<222> LOCATION: (4)..(4)
<223> OTHER INFORMATION: SULFATATION (sulfo tyrosine)
<220> FEATURE:
<221> NAME/KEY: MOD_RES
<222> LOCATION: (6)..(6)
<223> OTHER INFORMATION: SULFATATION (sulfo tyrosine)
<220> FEATURE:
<221> NAME/KEY: MOD_RES
<222> LOCATION: (8)..(8)
<223> OTHER INFORMATION: SULFATATION (sulfo tyrosine)
<220> FEATURE:
<221> NAME/KEY: MOD_RES
<222> LOCATION: (10)..(10)
<223> OTHER INFORMATION: SULFATATION (sulfo tyrosine)
<220> FEATURE:
<221> NAME/KEY: MOD_RES
<222> LOCATION: (12)..(12)
<223> OTHER INFORMATION: SULFATATION (sulfo tyrosine)

<400> SEQUENCE: 18

Ser Tyr Asp Tyr Ser Tyr Asp Tyr Ser Tyr Asp Tyr Ser
1               5                   10

<210> SEQ ID NO 19
<211> LENGTH: 13
<212> TYPE: PRT
<213> ORGANISM: artificial
<220> FEATURE:
<223> OTHER INFORMATION: anionic polypeptide
<220> FEATURE:
<221> NAME/KEY: VARIANT
<222> LOCATION: (2)..(2)
<223> OTHER INFORMATION: Tyr can be replaced by sulfotyrosine, tyrosine
      sulfonate, aminosuberic acid, and p-carboxymethyl phenylalanine
<220> FEATURE:
<221> NAME/KEY: VARIANT
<222> LOCATION: (4)..(4)
<223> OTHER INFORMATION: Tyr can be replaced by sulfotyrosine, tyrosine
      sulfonate, aminosuberic acid, and p-carboxymethyl phenylalanine
<220> FEATURE:
<221> NAME/KEY: VARIANT
<222> LOCATION: (6)..(6)
<223> OTHER INFORMATION: Tyr can be replaced by sulfotyrosine, tyrosine
      sulfonate, aminosuberic acid, and p-carboxymethyl phenylalanine
<220> FEATURE:
<221> NAME/KEY: VARIANT
<222> LOCATION: (8)..(8)
<223> OTHER INFORMATION: Tyr can be replaced by sulfotyrosine, tyrosine
      sulfonate, aminosuberic acid, and p-carboxymethyl phenylalanine
<220> FEATURE:
<221> NAME/KEY: VARIANT
<222> LOCATION: (10)..(10)
<223> OTHER INFORMATION: Tyr can be replaced by sulfotyrosine, tyrosine
      sulfonate, aminosuberic acid, and p-carboxymethyl phenylalanine
<220> FEATURE:
<221> NAME/KEY: VARIANT
<222> LOCATION: (12)..(12)
<223> OTHER INFORMATION: Tyr can be replaced by sulfotyrosine, tyrosine
      sulfonate, aminosuberic acid, and p-carboxymethyl phenylalanine

<400> SEQUENCE: 19

Ser Tyr Asp Tyr Ser Tyr Asp Tyr Ser Tyr Asp Tyr Ser
1               5                   10

<210> SEQ ID NO 20
<211> LENGTH: 26
<212> TYPE: PRT
<213> ORGANISM: artificial

```
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: MOD_RES
<222> LOCATION: (20)..(20)
<223> OTHER INFORMATION: D-proline
<220> FEATURE:
<221> NAME/KEY: misc_feature
<222> LOCATION: (22)..(22)
<223> OTHER INFORMATION: Phe is a 4-cyclohexylmethoxy-L-phenylalanine

<400> SEQUENCE: 20

Asn Leu His Lys Cys Gln Leu Arg Cys Ser Ser Leu Gly Leu Leu Gly
1               5                   10                  15

Arg Cys Ala Pro Thr Phe Cys Ala Cys Val
            20                  25

<210> SEQ ID NO 21
<211> LENGTH: 26
<212> TYPE: PRT
<213> ORGANISM: artificial
<220> FEATURE:
<223> OTHER INFORMATION: CD4 derived peptide
<220> FEATURE:
<221> NAME/KEY: BINDING
<222> LOCATION: (1)..(1)
<223> OTHER INFORMATION: TPA-Asn
<220> FEATURE:
<221> NAME/KEY: MOD_RES
<222> LOCATION: (20)..(20)
<223> OTHER INFORMATION: D-proline
<220> FEATURE:
<221> NAME/KEY: misc_feature
<222> LOCATION: (22)..(22)
<223> OTHER INFORMATION: Phe is a 4-cyclohexylmethoxy-L-phenylalanine

<400> SEQUENCE: 21

Asn Leu His Lys Cys Gln Leu Arg Cys Arg Ser Leu Gly Leu Leu Gly
1               5                   10                  15

Arg Cys Ala Pro Thr Phe Cys Ala Cys Val
            20                  25
```